US011865341B2

(12) United States Patent
Schulhauser et al.

(10) Patent No.: US 11,865,341 B2
(45) Date of Patent: *Jan. 9, 2024

(54) OBSTRUCTIVE AND CENTRAL SLEEP APNEA COMBINATION THERAPY CONTROL

(71) Applicant: Medtronic, Inc., Minneapolis, MN (US)

(72) Inventors: Randal C. Schulhauser, Phoenix, AZ (US); Avram Scheiner, Vadnais Heights, MN (US); Linnea R. Lentz, Stacy, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/180,705

(22) Filed: Mar. 8, 2023

(65) Prior Publication Data

US 2023/0218899 A1    Jul. 13, 2023

Related U.S. Application Data

(63) Continuation of application No. 17/930,645, filed on Sep. 8, 2022, now Pat. No. 11,623,089, which is a (Continued)

(51) Int. Cl.
*A61N 1/36* (2006.01)
*A61B 5/318* (2021.01)
(Continued)

(52) U.S. Cl.
CPC ............ *A61N 1/3606* (2013.01); *A61B 5/053* (2013.01); *A61B 5/0816* (2013.01); *A61B 5/318* (2021.01);
(Continued)

(58) Field of Classification Search
CPC .. A61N 1/3606; A61N 1/3614; A61N 1/0548; A61N 1/0551; A61B 5/318;
(Continued)

(56) References Cited

U.S. PATENT DOCUMENTS 6,240,316 B1    5/2001  Richmond et al.
6,928,324 B2    8/2005  Park et al.
(Continued)

FOREIGN PATENT DOCUMENTS

CN    202505987 U    10/2012
EP    1656181 B1     6/2008
WO    2010057286 A1  5/2010

OTHER PUBLICATIONS

Global Strategy for the Diagnosis, Management, and Prevention of COPD (Gold) 2018 Report, 2018 Global Initiative for Chronic Obstructive Lung Disease, Inc., 2018 (Applicant points out, in accordance with MPEP 609.04(a), that the year of publication, 2018, is sufficiently earlier than the effective U.S. filing date, so that the particular month of publication is not in issue.), 142 pp.
(Continued)

*Primary Examiner* — Ankit D Tejani
*Assistant Examiner* — Joshua Brendon Solomon
(74) *Attorney, Agent, or Firm* — Shumaker & Sieffert, P.A.

(57) ABSTRACT

An example method includes receiving one or more physiological signals; detecting an apnea event based on the one or more physiological signals; determining that the apnea event cannot be characterized as one of a normal, OSA (obstructive sleep apnea), CSA (central sleep apnea), or combination OSA/CSA event; and outputting an electrical stimulation as a default based on determining that the apnea event cannot be characterized as a normal event, an OSA event, a CSA event, or combination OSA/CSA events.

20 Claims, 10 Drawing Sheets

Related U.S. Application Data continuation of application No. 17/194,943, filed on Mar. 8, 2021, now Pat. No. 11,464,977.

(60) Provisional application No. 62/993,178, filed on Mar. 23, 2020.

(51) Int. Cl.
| *A61B 5/053* | (2021.01) |
| *A61N 1/05* | (2006.01) |
| *A61B 5/00* | (2006.01) |
| *A61B 5/08* | (2006.01) |

(52) U.S. Cl.
CPC .......... *A61B 5/4818* (2013.01); *A61N 1/0548* (2013.01); *A61N 1/0551* (2013.01); *A61N 1/3614* (2017.08); *A61B 2562/0219* (2013.01)

(58) Field of Classification Search
CPC ..... A61B 5/053; A61B 5/0816; A61B 5/4818; A61B 2562/0219
See application file for complete search history.

(56) References Cited

U.S. PATENT DOCUMENTS

| 6,999,817 | B2 | 2/2006 | Park et al. |
| 7,130,687 | B2 | 10/2006 | Cho et al. |
| 7,149,574 | B2 | 12/2006 | Yun et al. |
| 7,225,021 | B1 | 5/2007 | Park et al. |
| 7,371,220 | B1 | 5/2008 | Koh et al. |
| 7,473,227 | B2 | 1/2009 | Hsu et al. |
| 7,510,531 | B2 | 3/2009 | Lee et al. |
| 7,672,728 | B2 | 3/2010 | Libbus et al. |
| 7,747,323 | B2 | 6/2010 | Libbus et al. |
| 8,612,005 | B2 | 12/2013 | Rezai et al. |
| 8,644,921 | B2 | 2/2014 | Wilson |
| 8,938,299 | B2 | 1/2015 | Christopherson et al. |
| 9,014,819 | B2 | 4/2015 | Lee et al. |
| 9,498,627 | B2 | 11/2016 | Rosenberg et al. |
| 9,586,048 | B2 | 3/2017 | Ternes et al. |
| 9,706,934 | B2 | 7/2017 | Wilson |
| 10,052,484 | B2 | 8/2018 | Bolea et al. |
| 10,406,366 | B2 | 9/2019 | Westlund et al. |
| 11,464,977 | B2 | 10/2022 | Schulhauser et al. |
| 11,623,089 | B2 * | 4/2023 | Schulhauser ........ A61N 1/3606 607/42 |
| 2007/0118180 | A1 | 5/2007 | Ni et al. |
| 2007/0239057 | A1 | 10/2007 | Pu et al. |
| 2010/0016749 | A1 | 1/2010 | Atsma et al. |
| 2010/0174335 | A1 | 7/2010 | Stahmann et al. |
| 2011/0061647 | A1 | 3/2011 | Stahmann et al. |
| 2015/0196766 | A1 | 7/2015 | Rosenberg et al. |
| 2020/0238084 | A1 | 7/2020 | Ignagni |
| 2021/0290957 | A1 | 9/2021 | Schulhauser et al. |
| 2023/0001200 | A1 | 1/2023 | Schulhauser et al. |

OTHER PUBLICATIONS

Upper Airway Stimulation (Inspire Therapy), Rush System, Retrieved from: https://www.rush.edu/services/test-treatment/inspire-therapy on Mar. 3, 2021, 1 pp.

Arzt et al., "Phenotyping of Sleep-Disordered Breathing in Patients With Chronic Heart Failure With Reduced Ejection Fraction-the SchlaHF Registry," Journal of the American Heart Association, vol. 6, No. 12, Dec. 2, 2017, 26 pp.

Augostini et al., "How to Implant a Phrenic Nerve Stimulator for Treatment of Central Sleep Apnea?," Journal of Cardiovascular Electrophysiology, vol. 30, No. 5, May 2019, pp. 792-799.

Costanzo et al., "Transvenous Neurostimulation for Central Sleep Apnoea: a Randomised Controlled Trial," www.Lancet, vol. 388, Sep. 3, 2016, pp. 974-982.

Donovan et al., "Prevalence and Characteristics of Central Compared to Obstructive Sleep Apnea: Analyses from the Sleep Heart Health Study Cohort," Sleep, vol. 39, No. 7, Jul. 1, 2016, pp. 1353-1359.

Guerrero et al., "Readmission for Acute Exacerbation within 30 Days of Discharge Is Associated with a Subsequent Progressive Increase in Mortality Risk in COPD Patients: A Long-Term Observational Study," PLOS One, Mar. 4, 2016, 15 pp.

Jacobs et al., "Early Hospital Readmissions after an Acute Exacerbation of Chronic Obstructive Pulmonary Disease In the Nationwide Readmissions Database," AnnalsATS, vol. 15, No. 7, Jul. 2018, pp. 837-845.

Javaheri et al., "Central Sleep Apnea, Right Ventricular Dysfunction, and Low Diastolic Blood Pressure Are Predictors of Mortality in Systolic Heart Failure," Journal of the American College of Cardiology, vol. 49, No. 20, May 22, 2007, pp. 2028-2034.

Javaheri et al., "Sleep Apnea Testing and Outcomes in a Large Cohort of Medicare Beneficiaries with Newly Diagnosed Heart Failure," American Journal of Respiratory and Critical Care Medicine, vol. 183, Feb. 15, 2011, pp. 539-546.

Javaheri, Shahrokh, "Basics of Sleep Apnea and Heart Failure," American College of Cardiology, Feb. 19, 2013, 9 pp.

Padeletti et al., "Coexistent Chronic Obstructive Pulmonary Disease and Heart Failure in the Elderly," International Journal of Cardiology, vol. 125, Jan. 28, 2008, pp. 209-215.

Prosecution History from U.S. Appl. No. 17/194,943, now issued U.S. Pat. No. 11,464,977, dated Mar. 15, 2022 through Jun. 7, 2022, 41 pp.

Prosecution History from U.S. Appl. No. 17/930,645, dated Dec. 22, 2022 through Feb. 6, 2023, 26 pp.

Slebos et al., "Safety and Adverse Events after Targeted Lung Denervation for Symptomatic Moderate to Severe Chronic Obstructive Pulmonary Disease (Airflow)," American Journal of Respiratory and Critical Care Medicine, vol. 200, No. 12, Dec. 15, 2019, pp. 1477-1486.

Thomas et al., "Differentiating Obstructive from Central and Complex Sleep Apnea Using an Automated Electrocardiogram-Based Method," Sleep, vol. 30, No. 12, Dec. 2007, pp. 1756-1769.

\* cited by examiner

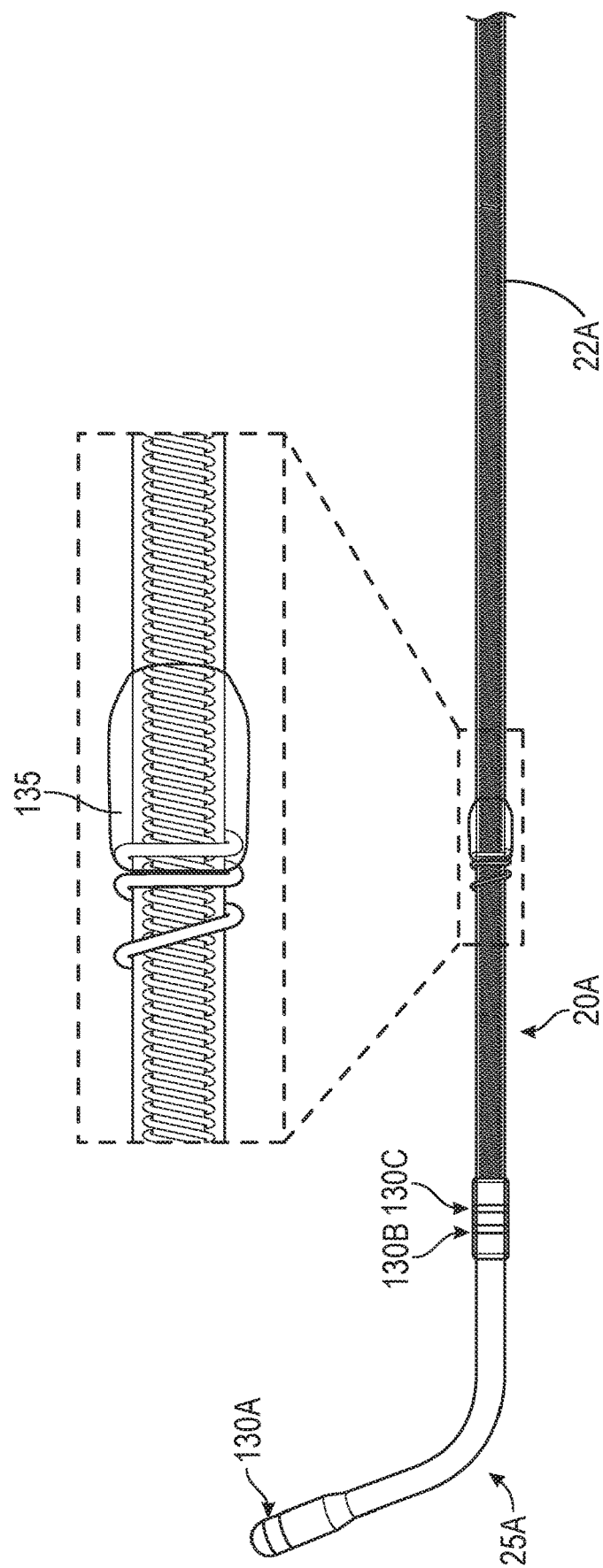

OBSTRUCTIVE AND CENTRAL SLEEP APNEA COMBINATION THERAPY CONTROL

This application is a continuation of U.S. patent application Ser. No. 17/930,645, filed 8 Sep. 2022, which is a continuation of U.S. patent application Ser. No. 17/194,943, filed 8 Mar. 2021, which claims the benefit of U.S. Provisional Patent Application No. 62/993,178, filed 23 Mar. 2020, the entire content of each application is incorporated herein by reference.

TECHNICAL FIELD

This disclosure relates to techniques for detection and treatment of sleep apnea and, more particularly, electrical stimulation for treatment of obstructive sleep apnea (OSA), central sleep apnea (CSA) and mixed apnea (i.e., both OSA & CSA).

BACKGROUND

Apnea is a relatively common form of disordered breathing characterized by interruptions to a patient's breathing. Often, the interruptions to breathing occur during sleep, at which time the disorder is called sleep apnea. Breathing cessation may occur numerous times during sleep, in some cases hundreds of times a night. Each cessation of breathing may last for up to a minute or longer.

Sleep apnea has multiple classifications based on the source of the dysfunction. For example, CSA results from neurological dysfunction, while OSA results form a mechanical blockage of the airway. The mechanical blockage may be due, for example, to fatty neck tissue compressing the trachea.

OSA, which encompasses apnea and hypopnea, is a serious disorder in which breathing is irregularly and repeatedly stopped and started during sleep, resulting in disrupted sleep and reducing blood oxygen levels. OSA is caused by complete or partial collapse of the pharynx during sleep. Muscles in a patient's throat intermittently relax thereby obstructing the upper airway while sleeping. Airflow into the upper airway may be obstructed by the tongue or soft pallet moving to the back of the throat and covering a smaller than normal airway. Loss of air flow also causes unusual interthoracic pressure as a person tries to breathe with a blocked airway. Lack of adequate levels of oxygen during sleep may contribute to abnormal heart rhythms, heart attack, heart failure, high blood pressure, stroke, memory problems and increased accidents. Additionally, loss of sleep occurs when a person is awakened during an apneic episode. Implantable medical devices capable of delivering electrical stimulation pulses have been proposed for treating OSA by electrically stimulating muscles around the upper airway that may block the airway during sleep and/or neurological structures innervating these muscles, such as the hypoglossal nerve.

Unlike OSA, CSA does not necessarily involve blockage of an airway. Instead, CSA involves failure of the brain to send appropriate signals to initiate action of the muscles required for respiration. CSA occurs during sleep when an acute increase in ventilation results in a decrease in the level of carbon dioxide in a patient's bloodstream (i.e., the $PaCO_2$). When the $PaCO_2$ falls below a threshold level required to stimulate breathing, the "central" (as in Central Nervous System) drive to respiratory muscles and airflow ceases, initiating central apnea. This apnea persists until the patient's $PaCO_2$ level rises above the threshold required to stimulate ventilation, upon which the cycle of hyperpnea followed by apnea may repeat. This is referred to as "periodic breathing". Implantable medical devices capable of delivering electrical stimulation pulses have been proposed for treating CSA by electrically stimulating neurological targets that control respiration, such as the phrenic nerve.

In a general population of patients diagnosed with sleep apnea, approximately 90% will have OSA and approximately 10% will have CSA. Approximately 5% will have Mixed OSA+CSA (i.e., exhibit both OSA and CSA at different times).

SUMMARY

The techniques of this disclosure generally relate to an implantable medical device (IMD) system and methods for delivering OSA, CSA, and combination OSA/CSA therapy. Therapy delivery circuitry, e.g., of an IMD, may be configured to deliver a first electrical stimulation via a first lead. The first lead may have a first plurality of electrodes. The therapy delivery circuitry may be configured to deliver second electrical stimulation via a second lead having a second plurality of electrodes. The IMD system may have processing circuitry configured to control the therapy delivery circuitry to deliver the first electrical stimulation configured to treat OSA and control the therapy delivery circuitry to deliver the second electrical stimulation configured to treat CSA. The first plurality of electrodes may be located along a distal portion of the first lead configured to be implanted within musculature of a tongue of a patient stimulating one or both hypoglossal nerves and/or motor points. The second plurality of electrodes may be located along a distal portion of the second lead configured to be implanted intravascularly proximate to a phrenic nerve within the patient.

In an example technique, a method includes receiving one or more physiological signals. Each of the one or more physiological signals may include respirations of a patient. Apnea events may be detected based on a primary biomarker in the one or more physiological signals. Each of the apnea events may be characterized as one of a normal event, an OSA event, a CSA event, or a combination OSA/CSA event based on a secondary biomarker in the one or more physiological signals. A first electrical stimulation provided may be configured to treat OSA in response to a first one or more of the apnea events being characterized as OSA events. A second electrical stimulation may be provided configured to treat CSA in response to a second one or more of apnea events being characterized as CSA events. A third electrical stimulation may be provided configured to treat combination OSA/CSA in response to a third one or more of the apnea events being characterized as combination OSA/CSA events.

In an example technique, a system may have therapy delivery circuitry configured to be coupled to a first lead comprising a first plurality of electrodes and a second lead comprising a second plurality of electrodes. The therapy delivery circuitry may deliver a first electrical stimulation via the first lead. The first electrical stimulation may be configured to treat OSA. A second electrical stimulation delivered via the second lead may be configured to treat CSA. Sensing circuitry may be configured to sense one or more physiological signals. Each of the one or more physiological signals may include respirations of a patient. Processing circuitry may be configured to detect apnea events based on timing of the respirations, determine at least one of a frequency spectrum or a morphology of the respirations based on the detection of the apnea events and characterize the apnea events as one of normal, OSA, CSA, or combination OSA/CSA events based on the at least one of the frequency spectrum or the morphology of the respirations. Based on the characterization of the apneas, the processing circuitry may control the therapy delivery circuitry to deliver one of no electrical stimulation, the first electrical stimulation, the second electrical stimulation, or both the first and second electrical stimulation in combination.

In an example technique, an implantable medical device may be configured to be coupled to a first lead comprising a first plurality of electrodes and a second lead comprising a second plurality of electrodes. The implantable medical device may have therapy delivery circuitry configured to deliver a first electrical stimulation via the first lead. The first electrical stimulation configured to treat OSA and a second electrical stimulation via the second lead configured to treat CSA. Sensing circuitry may be configured to sense one or more physiological signals. Processing circuitry may be configured to detect respirations in the one or more physiological signals, detect an apnea event based on the respirations detected in the one or more sensed physiological signals and characterize the apnea as one of obstructive sleep apnea (OSA), central sleep apnea (CSA), or mixed sleep apnea (OSA/CSA) based on at least one of a frequency spectrum or a morphology of the respirations. Based on the characterization of the apneas, the processing circuitry may control the therapy delivery circuitry to deliver one of the first electrical stimulation, the second electrical stimulation, or both the first and second electrical stimulation in combination.

The details of one or more examples of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIGS. 4A and 4B are conceptual diagrams of example electrical leads used for stimulation of the phrenic nerve in delivering CSA therapy according to one or more examples.

DETAILED DESCRIPTION

A medical device system for delivering electrical stimulation to the protrusor muscles of the tongue for the treatment of OSA, to the phrenic nerve for the treatment of CSA, and to both the protrusor muscles and the phrenic nerve for the treatment of combination OSA/CSA is described herein.

In general, the disclosure is directed to techniques for detecting and monitoring the respiratory function of a patient, e.g., based on detection of abnormal breathing patterns. In some examples, abnormal breathing patterns or other changes in patient status are detected based on accelerometer signals, cardiac electrogram, electrocardiogram (ECG), or other cardiac electrical signals, and/or impedance signals. Examples of this disclosure involve monitoring physiological signals, such as accelerometer signals, subcutaneous ECG signals and/or bioimpedance signals, using a subcutaneous IMD. In some examples, a subcutaneous IMD may use single source physiologic signal, such as an accelerometer signal, a subcutaneous ECG signal, or a bioimpedance signal, or combine them in any manner to improve detection sensitivity. In general, the physiological signal may be able to provide diagnostic information about physical parameters including respiratory rate, respiratory breathing anomalies and sleep apnea. For example, respiratory anomalies such as OSA, CSA or respiratory patterns associated with mixed OSA/CSA may be detected with a subcutaneous sensor placed on the thorax which may detect changes in respiratory rate or respiratory depth, cessation of respiration, and/or other respiratory characteristics associated with apnea. In some examples, respiratory parameters associated with "normal" or "healthy" respiration may also be identified.

Figure 1:
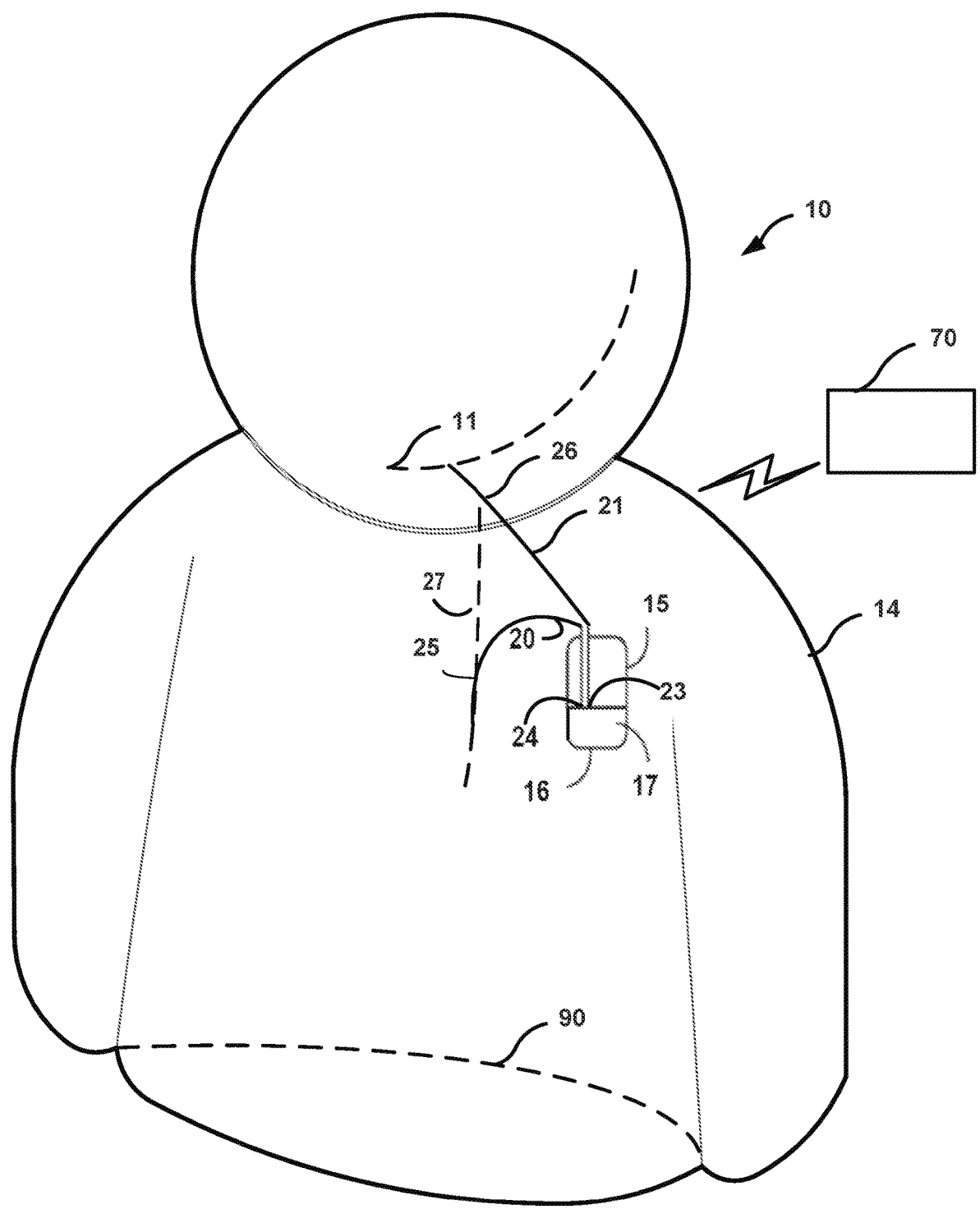
FIG. 1 is a conceptual diagram of an IMD system for delivering OSA, CSA and/or mixed OSA/CSA therapy according to one or more examples.

FIG. 1 is a conceptual diagram of a medical system for delivering OSA, CSA and/or mixed OSA/CSA therapy. In system 10, IMD 16 and leads 20, 21 are implanted in patient 14. In an example, it is possible to provide both OSA and CSA therapy using a single IMD 16.

IMD 16 includes housing 15 enclosing circuitry of IMD 16. In some examples, IMD 16 includes connector assembly 17, which is hermetically sealed to housing 15 and includes one or more connector bores for receiving medical electrical leads 20 and or 21 used for delivering CSA and OSA therapy, respectively. Although two leads 20 and 21 are illustrated in FIG. 1, there may be more than leads 20, 21 to which IMD 16 is coupled. For example, an adaptor may be used to provide for two or more leads extending from one connector bore (not shown) on connector assembly 17.

Figure 2:
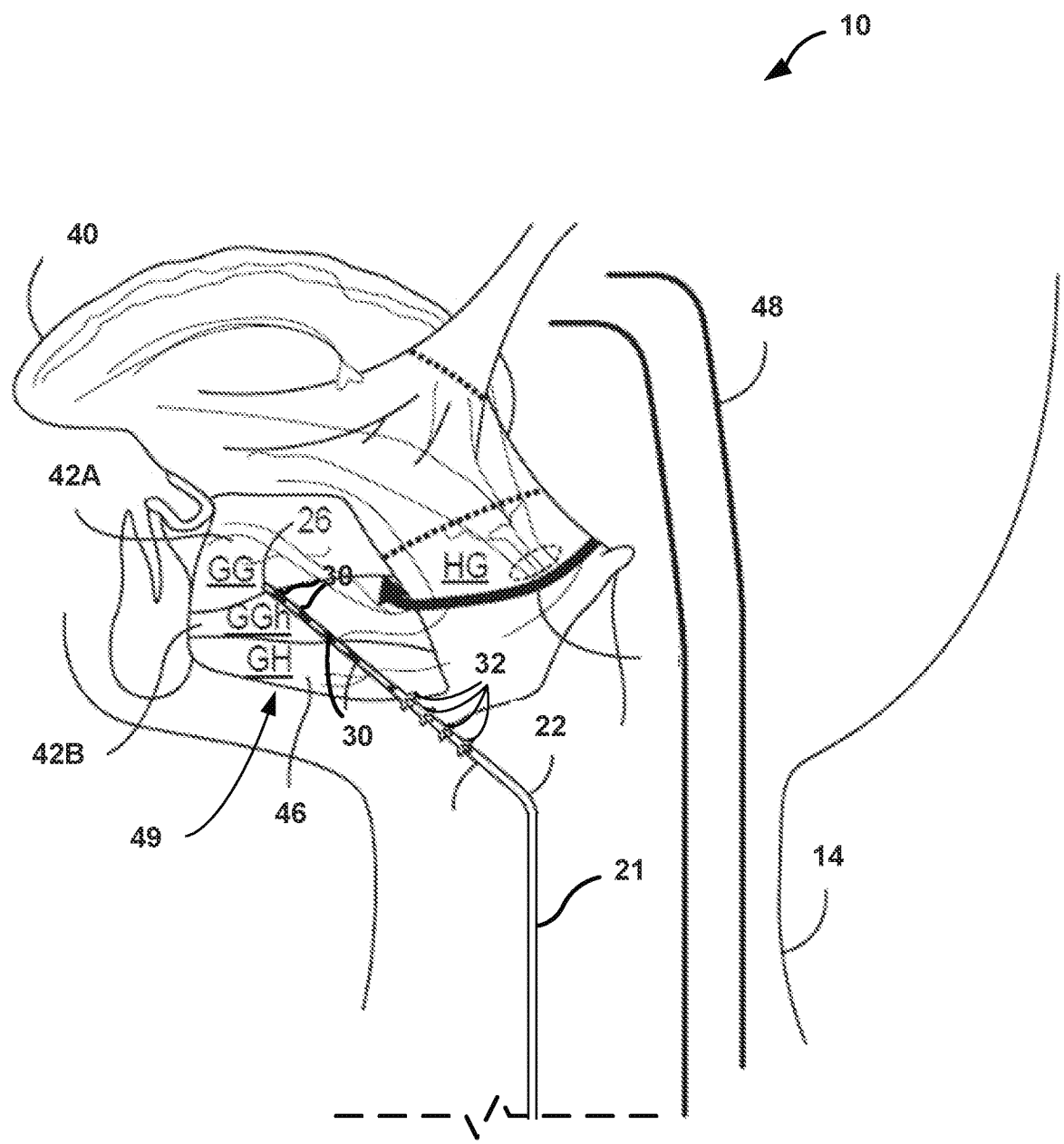
FIG. 2 is a conceptual diagram of an example lead for delivering OSA therapy according to one or more examples.

Lead 21 has a proximal end 23 coupled to connector assembly 17 and a distal end 26. Distal end 26 is located at or near one or more motor points, one or more protrusor muscles or hypoglossal nerves 11, and/or motor points 54A, 54B, 55A and 55B (FIG. 3), e.g., one or more locations where axons of the hypoglossal nerve 11 terminate at respective muscle fibers of the protrusor muscles 42 and/or 46 (FIG. 2). Lead 20 also has a proximal end 24, which is coupled within connector assembly 17, and a distal portion 25, which extends near phrenic nerve(s) 27 for delivering CSA therapy. FIG. 1 illustrates lead 20 located at or near one of two phrenic nerves so electrodes, e.g., electrodes 130 of FIGS. 4A and 4B, could be used to provide therapeutic stimulation to one or both of phrenic nerves 27. Using a subclavian approach, electrical lead 20 may be placed in the left pericardiophrenic vein.

In some examples, system 10 may be an asynchronous system. In some examples, system 10 is a synchronous system. Synchronous, for the purposes of the present disclosure may relate to synchronizing or coordinating therapy with a patient's breathing.

Figure 5:
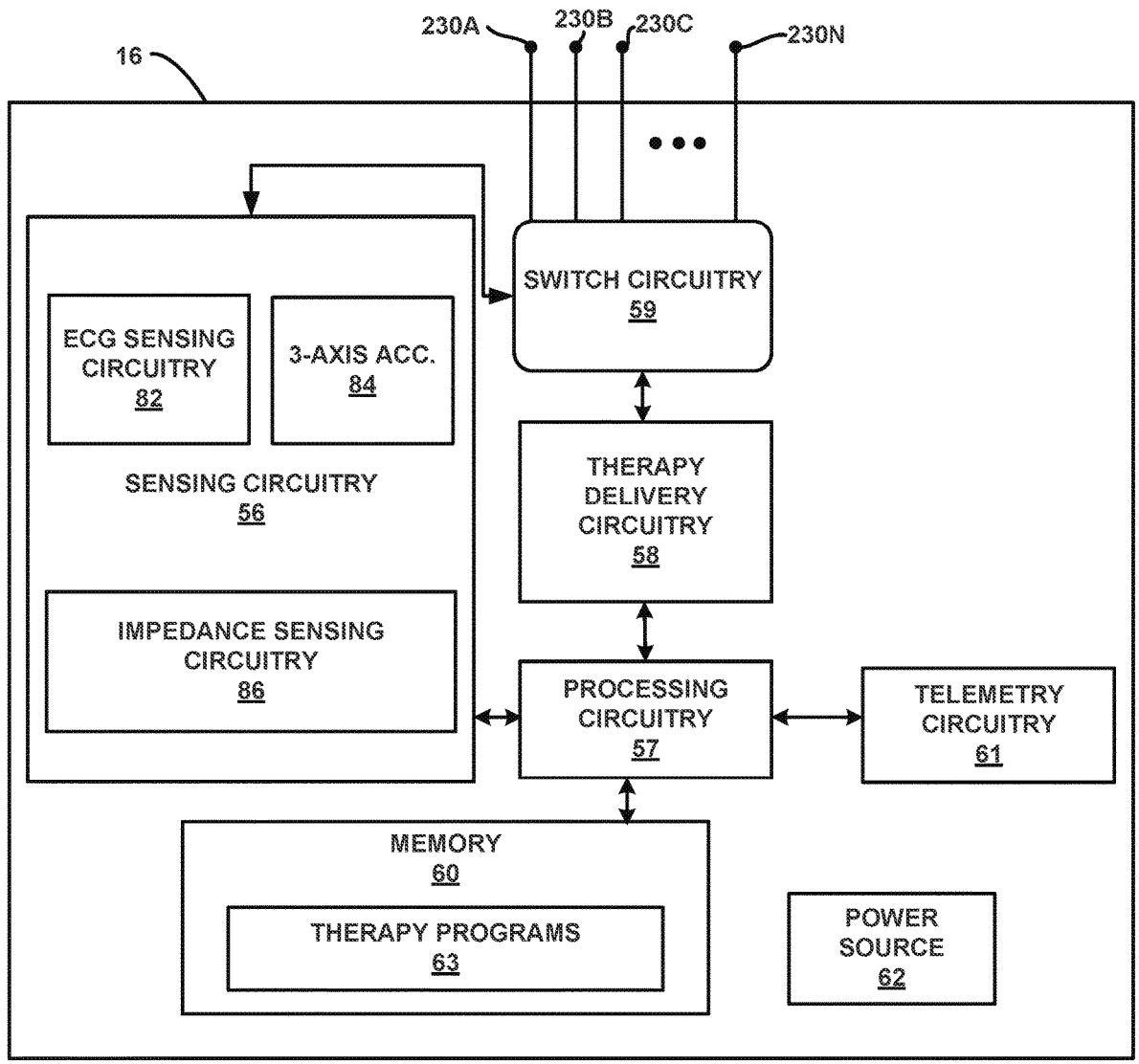
FIG. 5 is block diagram illustrating example configurations of implantable medical devices (IMDs) which may be utilized in the system of FIG. 1.

Additionally, processing circuitry of system 10 may control the delivery of therapy, e.g., turn the stimulating therapy on and off, based on sensing feedback from sensing circuitry 56 (FIG. 5). The sensing feedback may indicate whether the patient is experiencing apneas. The sensing feedback may further allow processing circuitry to classify the patient's respiration, e.g., the apneas, as OSA, CSA, or mixed OSA/CSA. In some examples, processing circuitry may further be configured to classify the patient's respiration as "healthy/normal" based on the sensing feedback, or may determine that the patient's respiration cannot be classified with a desired degree of confidence, and may turn off therapy or deliver a default or safety mode therapy, respectively, in response to these additional classifications.

Figure 4B:
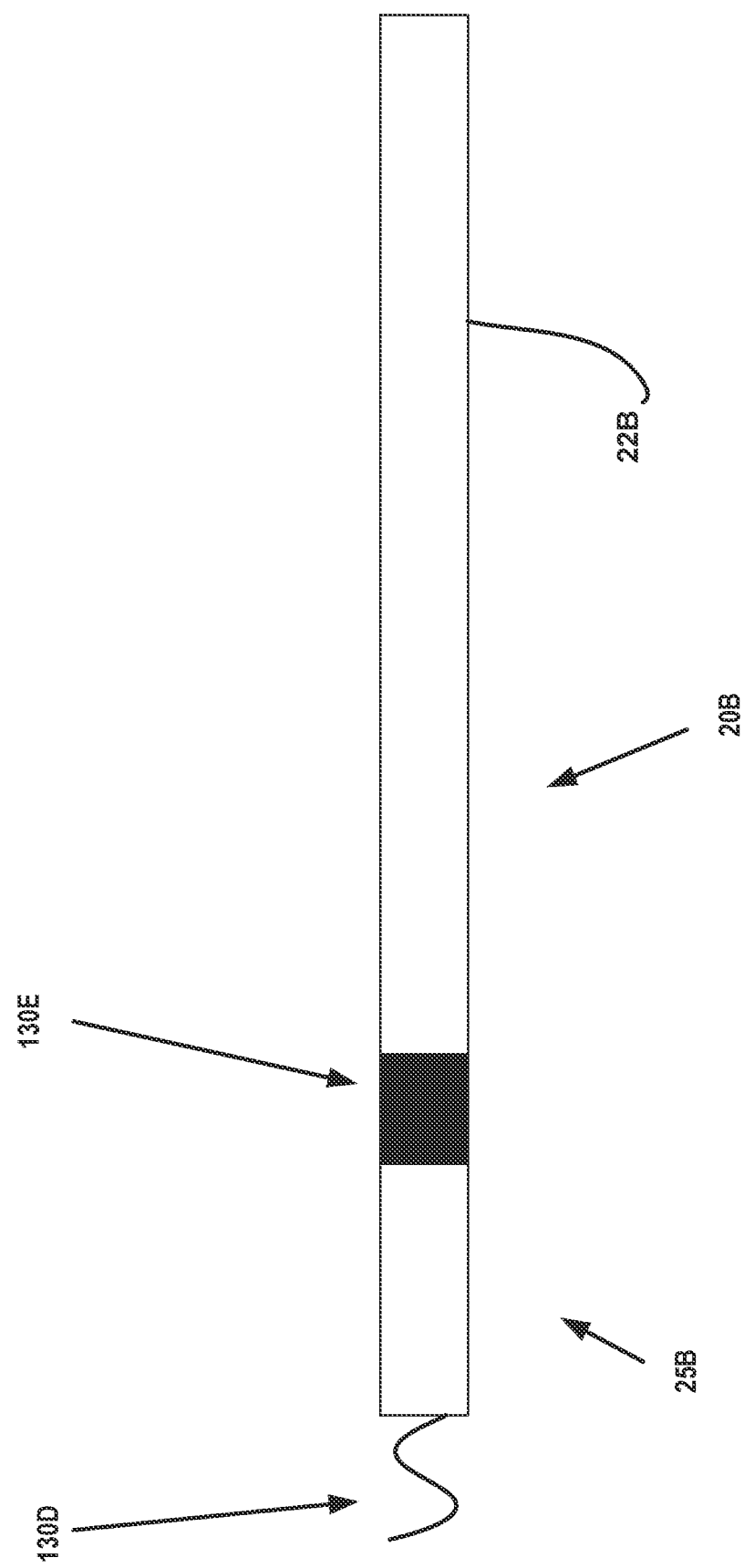

As discussed, sleep apnea has two primary manifestations; OSA and CSA. In a general population of patients diagnosed with sleep apnea, approximately 92% will have OSA, approximately 3% will have CSA and approximately 5% will have MIXED apneas (i.e., the patients will exhibit both OSA and CSA at different times). For heart failure (HF) patients diagnosed with sleep apnea, approximately 54% will have OSA, approximately 6% will have CSA and approximately 40% will have MIXED apneas. The techniques of this disclosure generally relate to IMD 16 delivering CSA, OSA and combination CSA/OSA therapy. Therapy delivery circuitry 58 (FIG. 5) of IMD 16 may be configured to deliver a first electrical stimulation via lead 21. Lead 21 may have a plurality of electrodes 30 (FIG. 2). A second electrical stimulation may be delivered via lead 20 having a plurality of electrodes 130 (FIGS. 4A and 4B). IMD 16 may have processing circuitry 52 (FIG. 5) configured to control therapy delivery circuitry 58 to deliver the first electrical stimulation configured to treat OSA and control therapy delivery circuitry 58 to deliver the second electrical stimulation configured to treat CSA. First plurality of electrodes 30 may be located along a distal portion 26 of lead 21 configured to be implanted within musculature of a tongue of patient 14. Second plurality of electrodes 130 may be located along distal portion 25 of lead 20 configured to be implanted intravascularly proximate to phrenic nerve(s) 27 within patient 14.

As illustrated in FIG. 1, system 10 includes an external device 70, which may be communicatively coupled to IMD 16. External device 70 may be a computing device, e.g., a hand-held computing device, that provides a user interface for a user to interface with IMD 16. The user may use external device 70 to retrieve information from IMD 16 regarding patient 14, e.g., diagnostic information regarding one or more conditions of patient 14, and/or the performance of IMD 16, e.g., delivery of therapy by the IMD or the condition of components of IMD 16. The user may also user external device 70 to program IMD 16, e.g., various sensing, analysis, or therapy parameters of IMD 16. External device 70 may be referred to as a "programmer" for IMD 16. External device may be a smartphone or tablet. External device 70 may be a local device coupled to IMD 16 by a wireless connection, or a remote device coupled to IMD 16 by a network including one or more wired and/or wireless connections.

FIG. 2 is a conceptual diagram of a lead for delivering OSA therapy according to one or more examples. Lead 21 may include a flexible, elongated lead body 22 extending from lead proximal end 23 to lead distal end 26. As illustrated, lead 20 includes one or more electrodes 30 carried along a lead distal portion adjacent lead distal end 26 and are configured for insertion within protrusor muscles 42A, 42B, and 46 of tongue 40. As one example, the genioglossus muscle includes oblique compartment 42A and horizontal compartment 42B. In this disclosure, the genioglossus muscle is referred to as protrusor muscle 42. Protrusor muscle 46 is an example of the geniohyoid muscle.

While protrusor muscles 42 and 46 are described, the example techniques described in this disclosure are not limited to stimulating protrusor muscles 42 and 46. Also, FIG. 2 illustrates one set of protrusor muscles 42 and 46 (e.g., on a first side of tongue 40). The other side of tongue 40 also includes protrusor muscles. For instance, a left side of tongue 40 includes a first set of protrusor muscles 42 and 46, and a right side of tongue 30 includes a second set of protrusor muscles.

In some examples, a surgeon may implant one or more leads 21 so one or more electrodes 30 are implanted within soft tissue, such as musculature, proximate to medial branches of one or both hypoglossal nerves 11. In some examples, one or more electrodes 30 may be approximately 5 millimeters (mm) from a major trunk of hypoglossal nerve 11. In some examples, one or more electrodes 30 may be placed in an area of protrusor muscles 42 and 46 including the motor points. This is where each nerve axon terminates in the muscle (also called the neuro-muscular junction). The motor points are not at one location but spread out in the protrusor muscles. One or more electrodes 30 may be generally in the area of the motor points so the motor points are within 1 to 10 mm from one or more electrodes 30. Examples of motor points for protrusor muscles 42 and 46 are illustrated in more detail with respect to FIG. 3.

Tongue 40 includes a distal end, e.g., tip of tongue 40, and electrodes 30 may be implanted proximate to the root of tongue 40. The surgeon may implant one or more leads 21 so one or more electrodes are implanted proximate to bottom surface 49 of tongue 40, as illustrated in FIG. 2. For example, the location for stimulation for genioglossus muscle 42 may be approximately 30 mm from the Symphysis of the jaw, e.g., where the genioglossus and hypoglossal muscles insert. The location for stimulation for geniohyoid muscle 46 may be approximately 40 mm from the Symphysis. For both genioglossus muscle 42 and geniohyoid muscle 44, the location for stimulation may be approximately 11 mm lateral to the midline on both the right and left sides of tongue 40 for stimulating respective hypoglossal nerves 11. In some examples, rather than stimulating hypoglossal nerves 11, the examples described in this disclosure may be configured for stimulating the motor points, as described in more detail with respect to FIG. 3. Stimulating the motor points may result in activation of the hypoglossal nerve 11 but may generally be stimulating at a different location than direct stimulation to the hypoglossal nerve 11 trunk or major branches. As a result, in some examples, simulation of one or more motor points may result in more precise activation of muscle fibers than may be possible with stimulation of the hypoglossal nerve trunk or major branches itself.

One or more electrodes 30 of lead 21 may be ring electrodes, segmented electrodes, partial ring electrodes or any suitable electrode configuration. Segmented and partial ring electrodes each extend along an arc less than 360 degrees, e.g., 90-120 degrees, around the outer perimeter of lead 21. In this manner, multiple segmented electrodes may be disposed around the perimeter of lead 21 at the same axial position of lead 21. In some examples, segmented electrodes may be useful for targeting different fibers of the same or different nerves at respective circumferential positions with respect to lead 21 to generate different physiological effects (e.g., therapeutic effects). In some examples, lead 21 may be, at least in part, paddle shaped, e.g., a "paddle" lead, and may include an array of electrodes on a common surface, which may or may not be substantially flat.

As described above, in some examples, electrodes 30 are within musculature of tongue 40. Accordingly, one or more electrodes 30 may be "intramuscular electrodes." Intramuscular electrodes may be different than other electrodes placed on or along a nerve trunk or branch, such as a cuff electrode, used to directly stimulate the nerve trunk or branch. The example techniques described in this disclosure are not limited to intramuscular electrodes and may be extendable to electrodes placed closer to a nerve trunk or branch of hypoglossal nerve(s) 11. Also, in some examples, rather than one or more electrodes 30 being "intramuscular electrodes," one or more electrodes 30 may be implanted in connective tissue or other soft tissue proximate to hypoglossal nerve 11.

In some examples, lead 21 may be configured for advancement through the soft tissue, which may include the protrusor muscle tissue, to anchor electrodes 30 in proximity of the hypoglossal nerve(s) innervating protrusor muscles 42 and/or 46, and/or motor points connecting axons of hypoglossal nerve(s) to respective muscle fibers of protrusor muscles 42 and/or 46. However, in some examples, lead 21 may be configured for advancement through vasculature of tongue 40. As one example, a surgeon may implant lead 21 in the lingual veins near hypoglossal nerve 11 though venous access in the subclavian vein. In such examples, one or more electrodes 30 may be "intravascular electrodes."

As described above, electrical stimulation therapy generated by IMD 16 and delivered via one or more electrodes 30 may activate protrusor muscles 42 and 46 to move tongue 40 forward, to promote a reduction in obstruction or narrowing of the upper airway 48 during sleep. As used herein, the term "activated" with regard to the electrical stimulation of protrusor muscles 42 and 46 refers to electrical stimulation causing depolarization or an action potential of the cells of the nerve. e.g., hypoglossal nerve(s) 11, or stimulation at the neuro-muscular junction between the nerve and the protrusor muscles, e.g., at the motor points, innervating protrusor muscles 42 and 46 and motor points and subsequent depolarization and mechanical contraction of the protrusor muscle cells of protrusor muscles 42 and 46. In some examples, protrusor muscles 42 and 46 may be activated directly by the electrical stimulation therapy.

Protrusor muscles 42 and/or 46, on a first side of tongue 40, e.g., left or right side of tongue 40), may be activated by a medial branch of a first hypoglossal nerve 11, and the protrusor muscles, on a second side of tongue 40, e.g., other of left or right side of tongue 40), may be activated by a medial branch of a second hypoglossal nerve. The medial branch of a hypoglossal nerve 11 may also be referred to as the XIIth cranial nerve. The hyoglossus and styloglossus muscles (not shown in FIG. 2), which cause retraction and elevation of tongue 40, are activated by a lateral branch of hypoglossal nerve 11.

One or more electrodes 30 may be used to deliver bilateral or unilateral stimulation to protrusor muscles 42 and 46 via the medial branch of the hypoglossal nerve or branches of hypoglossal nerve 11, e.g. such as at the motor point where a terminal branch of the hypoglossal nerve interfaces with respective muscle fibers of protrusor muscles 42 and/or 46. For example, one or more electrodes 30 may be coupled to output circuitry of IMD 16 to enable delivery of electrical stimulation pulses in a manner selectively activating the right and left protrusor muscles in a cyclical or alternating pattern to avoid muscle fatigue while maintaining upper airway patency. Additionally, or alternatively, IMD 16 may deliver electrical stimulation to selectively activate protrusor muscles 42 and/or 46, or portions of protrusor muscles 42 and/or 46, during unilateral stimulation of the left or right protrusor muscles.

For instance, in some examples, one lead 21 may be implanted so one or more of electrodes 30 deliver electrical stimulation to stimulate the left hypoglossal nerve or motor points of protrusor muscles on the left side of tongue, and therefore cause the left protrusor muscles to activate. In such examples, the electrical stimulation from one or more electrodes 30 may not be of sufficient amplitude to stimulate the right hypoglossal nerve or motor points of protrusor muscles on the right side of tongue and cause the right protrusor muscles to activate. In some examples, one lead 21 may be implanted so one or more of electrodes 30 deliver electrical stimulation to stimulate the right hypoglossal nerve or motor points of protrusor muscles on the right side of tongue, and therefore cause the right protrusor muscles to activate. In such examples, the electrical stimulation from one or more electrodes 30 may not be of sufficient amplitude to stimulate the left hypoglossal nerve or motor points of protrusor muscles on the left side of tongue and cause the left protrusor muscles to activate. Accordingly, in some examples, an adaptor may be used to apply two leads like lead 21 to stimulate each of the left and right hypoglossal nerves.

In some examples, one lead 21 may be implanted substantially in the middle (e.g., center) of tongue 40. In such examples, one or more electrodes 30 may deliver electrical stimulation to both hypoglossal nerves or motor points of both muscles on the both sides of tongue 40 causing both hypoglossal nerves or motor points to activate respective left and right protrusor muscles. It may be possible to utilize current steering and field shaping techniques so one or more electrodes 30 deliver a first electrical stimulation stimulating the left hypoglossal nerve or motor points of protrusor muscles on the left side of tongue 40 with little to no stimulation of the right hypoglossal nerve or motor points of protrusor muscles on the right side of tongue, and then one or more electrodes 30 deliver a second electrical stimulation stimulating the right hypoglossal nerve or motor points of protrusor muscles on the right side of tongue with little to no stimulation of the left hypoglossal nerve or motor points of protrusor muscles on the left side of tongue. In examples where two leads like lead 21 are utilized, each lead may alternate delivery of stimulation to respective hypoglossal nerves or motor points. In this way, IMD 16 may stimulate one hypoglossal nerve 11 or one set of motor points and then the other hypoglossal nerve or another set of motor points, which may reduce muscle fatigue.

For instance, continuous stimulation may cause protrusor muscles to be continuously in a protruded state. This continuous contraction may cause protrusor muscles 42 and/or 46 to fatigue. In such cases, due to fatigue, the stimulation may not cause protrusor muscles 42 and/or 46 to maintain a protruded state (or higher intensity of the electrical stimulation may be needed to cause protrusor muscles 42 and/or 46 in the protruded state). By stimulating one set of protrusor muscles, e.g., left or right, a second set, e.g., other of left or right, of protrusor muscles may be at rest. Stimulation may then alternate to stimulate the protrusor muscles that were at rest and thereby maintain protrusion of tongue 40, while permitting the protrusor muscles 42 and/or 46 that were previously activated to rest. Hence, by cycling between alternate stimulation of the left and right protrusor muscles, tongue 40 may remain in the protruded state, while one of the first or second set of protrusor muscles is at rest. In some examples, one lead 21 may be implanted laterally or diagonally across tongue 40 so some of electrodes 30 may be used to stimulate the left hypoglossal nerve 11 and/or motor points of the protrusor muscles on the left side of tongue 40 and some of electrodes 30 may be used to stimulate the right hypoglossal nerve and/or motor points of the protrusor muscles on the right side of tongue 40. In such examples, IMD 16 may selectively deliver electrical stimulation to a first hypoglossal nerve and/or first motor points of the protrusor muscles on the a first side of tongue 40 via a first set of one or more electrodes 30, and then deliver electrical stimulation to a second hypoglossal nerve and/or/or second set of motor points of the protrusor muscles on a second side of tongue 40 via a second set of one or more electrodes 30. This may be another way in which to reduce muscle fatigue. Additional methods to reduce muscle fatigue include waveform variations, e.g., rectangle, sawtooth, triangle, or biphasic, and/or any technique to manipulate the electrical field to vary recruitment of nerve fibers.

Lead proximal end 24 includes a connector (not shown in FIG. 2) coupled to connector assembly 17 of IMD 16 to provide electrical connection between circuitry enclosed by housing 15 of IMD 16. Elongated lead body 22 encloses electrical conductors extending from each of one or more electrodes 30 to the proximal connector at proximal end 24 to provide electrical connection between output circuitry of IMD 16 and the electrodes 30.

There may be various ways in which lead 21 is implanted in patient 14. As one example, a surgeon may insert a needle (also called introducer needle) through below the jaw and in tongue 40 starting from the back of tongue 40. The surgeon may insert the needle until the needle reaches proximate to the tip of tongue 40, angling the needle to be proximate to the hypoglossal nerve 11, e.g., left or right hypoglossal nerve 11, and to the motor points. In some examples, the needle may include one or more electrodes at the distal end, and the surgeon may cause the one or more electrodes of the needle to output an electrical stimulation, which in turn causes a physiological response such as activation of protrusor muscles 42 and/or 46 and protrusion of tongue 40. The surgeon may adjust the location of the needle based on the physiological response to determine a location in tongue 40 providing effective treatment. Using a needle with stimulating electrodes is not necessary in every example.

Once the needle is in place, the surgeon may insert a guidewire (or simply "guide") through the needle and anchor the guidewire to tissue of tongue 40. Then, the surgeon may remove the needle.

The surgeon may place an introducer, which may or may not include a dilator, over the guidewire through the opening created by the needle. The introducer may be referred to as an introducer, introducer sheath, or introducer/dilator. In some examples, the introducer may optionally include one or more electrodes the surgeon may use to stimulate tongue 40 to ensure lead 21 will be located in the correct location, relative to the target nerve tissue. e.g., motor points. Once the introducer is in place, the surgeon may remove the guidewire. In some examples, the introducer may be flexible or curved to ease placement of the introducer in patient 14.

The surgeon may put lead 21 through the introducer so one or more electrodes 30 are proximate to hypoglossal nerve 11 (e.g., so distal end 26 is near tip of tongue as one non-limiting example). Electrodes 30 may be proximate to hypoglossal nerve 11 and/or motor points of the protrusor muscles due to the needle creating an opening near hypoglossal nerve 11 and/or motor points of the protrusor muscle. The surgeon may then tunnel proximal end 24 of lead 21 back to a connection with IMD 16.

In this manner, the surgeon may implant one lead 21. In examples where two or more leads are implanted, the surgeon may perform steps similar to those described above.

FIG. 1 illustrates the location of IMD 16 as being in the left or right pectoral region. For instance, the surgeon may plan on implanting IMD 16 in the left pectoral region unless another medical device is already implanted in the left pectoral region. The surgeon may then implant IMD 16 in the right pectoral region. There may be other locations where the surgeon may implant IMD 16 such as the back of patient 14. The example techniques are not limited to any particular implant location of IMD 16. Further, an adaptor may be used to provide for two leads, e.g., positioned bilaterally, which may be positioned in a right and left side of the patient's hypoglossal nerve 11, protrusor muscles 42 and/or 46 or one or more motor points 54A, 54B, 55A and/or 55B.

Elongated lead body 22 may be a flexible lead body through which insulated electrical conductors extend to respective electrodes 30. The distal most electrode 30 may be adjacent or proximate to lead distal end 26. Each of electrodes 30 may be spaced proximally from the respective adjacent one of electrodes 30 by respective interelectrode distances.

In some examples, housing 15 of IMD 16 may include an electrode functioning as a cathode or anode as part of a cathode/anode pair with one of electrodes 30. In some examples, housing 15 itself may function as the cathode or anode.

Each of electrodes 30 is a circumferential ring electrode which may be uniform in diameter with elongated lead body 22. As described above, electrodes 30 may include other types of electrodes such as a tip electrode, e.g., electrode 130A (FIG. 4A), a helical electrode, e.g., electrode 130D (FIG. 4B), a coil electrode, a segmented electrode, or a button electrode as examples.

Lead 21 may include one or more fixation members 32 for minimizing the likelihood of lead migration. Fixation member 32 may include multiple sets of tines which engage the surrounding tissue when lead distal portion 28 is positioned at the target therapy delivery site. Tines of fixation member 32 may extend radially and proximally at an angle relative to a longitudinal axis of lead body 22 to prevent or reduce retraction of lead body 22. Tines of fixation member 32 may be collapsible against elongated lead body 22 when lead 21 is held within the confines of a lead delivery tool, e.g., a needle or introducer, used to deploy lead distal portion 26 at the target implant site. In some examples, fixation member 32 may additionally or alternatively include one or more hooks, barbs, helices, or other fixation mechanisms extending from one or more longitudinal locations along elongated lead body 22 and/or lead distal end 26. Additional fixation techniques may incorporate the use of bioabsorbable coatings, e.g., sucrose, alginate, etc., when used after acute implantation, dissolve away so as to expose the anchoring feature, e.g., hooks, barbs, helices, micro-needle surfacing, or other fixation mechanisms.

Fixation members 32 may partially or wholly engage one or more of protrusor muscles 42 and/or 46, one or more motor points 54A, 54B, 55A and/or 55B, and/or other muscles below tongue 40, and/or other soft tissues of the neck, e.g., fat and connective tissue, when proximal end of lead body 22 is tunneled to an implant pocket of IMD 16. In some examples, fixation member 32 may include one or more fixation mechanisms located at other locations, including at or proximate to distal end 26, between electrodes 30, or otherwise more distally or more proximally than the location shown in FIG. 2.

The implant pocket of IMD 16 may be in a pectoral region of patient 14. Accordingly, the length of lead body 22 from distal portion 26 to lead proximal end 24 may be selected to extend from a target therapy delivery site in protrusor muscles 42 and/or 46 to a location in the pectoral region where IMD 16 is implanted. The length may be up to 10 centimeters (cm) or up to 20 cm as examples but may generally be 25 cm or less, though longer or shorter lead body lengths may be used depending on the anatomy and size of patient 14.

In some examples, an IMD 16 having a lead 21 with a proximal end 24 and a distal end 26 defines lead body 22 with electrodes 30 disposed on lead 21. In other examples, a fixation member 32 may be disposed on lead body 22 of lead 21. Fixation member 32 may be configured to secure lead 21 to tissue within a patient 14. Fixation member 32 may be disposed on lead 21 at a location proximal to electrodes 30 of lead 21.

Figure 3:
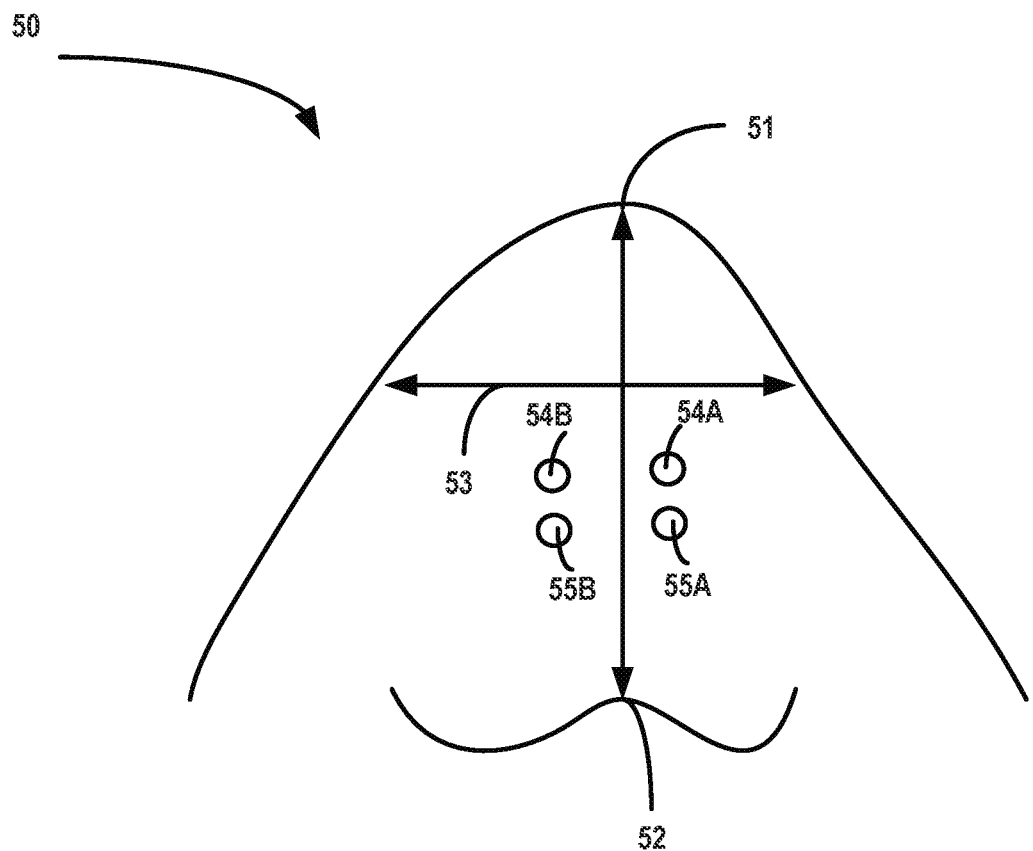
FIG. 3 is a conceptual diagram illustrating example locations of motor points where stimulation for OSA therapy may be delivered.

FIG. 3 is a conceptual diagram illustrating example locations of motor points where stimulation for OSA therapy may be delivered. FIG. 3 illustrates jaw 50 of patient 14, where patient 14 is in a supine position and jaw 50 of patient 14 is viewed from an inferior location of patient 14. For instance, FIG. 3 illustrates symphysis 51 and hyoid bone 52. In the example illustrated in FIG. 3, the line interconnecting symphysis 51 and hyoid bone 52 may be considered as a y-axis along the midline of tongue 40. FIG. 3 also illustrates intergonial distance 53 between the two gonia of patient 14, where the gonia is a point on each side of the lower jaw 50 at the mandibular angle. Intergonial distance 53 may be along the x-axis of tongue 40.

FIG. 3 illustrates motor points 54A and 54B and motor points 55A and 55B. Motor points 54A may be motor points for the right genioglossus muscle, and motor points 54B may be motor points for the left genioglossus muscle. Motor points 55A may be motor points for the right geniohyoid muscle, and motor points 55B may be motor points for the left geniohyoid muscle. Motor points 54A and 54B and motor points 55A and 55B may genericize the motor points for each muscle for purposes of illustration. There may be additional motor points and/or motor points at different locations for each muscle.

In one or more examples, lead 21 and/or one or more electrodes 30 may be implanted proximate to motor points 54A, 54B, 55A, or 55B for stimulating at motor points 54A, 54B, 55A, and/or 55B. For instance, in examples where two leads are implanted, a first lead and its electrodes may be implanted proximate to motor points 54A and/or 55A and a second lead and its electrodes may be implanted proximate to motor points 54B and/or 55B. In one or more examples, electrodes 30 may be approximately 1 mm to 10 mm from respective motor points 54A, 54B, 55A, or 55B.

A hypoglossal nerve 11, e.g., on the left or right side of tongue 40, initially is a trunk of nerves fibers called axons. The axons of hypoglossal nerve 11 branch out. For example, the trunk of hypoglossal nerve 11 includes multiple sets of axons including a first set of axons, and the first set of axons branch out from the trunk of hypoglossal nerve 11. The first set of axons include multiple groups of axons including a first group of axons, and the first group of axons branch out from the first set of axons, and so forth. The locations where the branched-out axons interface with respective muscle fibers of protrusor muscles 42 and/or 46, e.g., genioglossus and/or geniohyoid muscle, are referred to as motor points.

For instance, a branch of hypoglossal nerve 11 interfacing, e.g., connects at the neuro-muscular junction, with the muscle fiber is referred to as a terminal branch, and the end of the terminal branch is a motor point. The length of a terminal branch may be approximately 10 mm from hypoglossal nerve 11 to the genioglossal or geniohyoid muscles. In some examples, there may be approximately an average of 1.5 terminal branches with a standard deviation of ±0.7 for the right geniohyoid muscle, an average of 4.8 terminal branches with a standard deviation of ±1.4 for the right genioglossus muscle, an average of 2.0 terminal branches with a standard deviation of +0.9 for the left geniohyoid muscle, and an average of 5.1 terminal branches with a standard deviation of +1.9 for the left genioglossus muscle.

There may be possible advantages with stimulating at motor points 54A, 54B, 55A, or 55B, as compared to some other techniques. For instance, some techniques utilize cuff electrodes or stimulate at hypoglossal nerve 11. Due to the different bifurcation patterns, placing a cuff electrode around hypoglossal nerve 11, or generally attaching an electrode to hypoglossal nerve 11 may be challenging. Also, where cuff electrodes or electrodes attach to hypoglossal nerve 11 are used, implanting electrodes around or at each of hypoglossal nerves 11 requires multiple surgical entry points to attached to both hypoglossal nerves. Moreover, utilizing cuff electrodes or electrodes attaching to hypoglossal nerves 11 may possibly negatively impact the nerve by tugging, stretching, or otherwise causing irritation. Accordingly, utilizing lead 21 and electrodes 30 implanted proximate to the motor points may be beneficial, e.g., less surgery to implant and less impact on the nerve, as compared to techniques where cuff electrodes or electrodes implanted on the hypoglossal nerve are utilized. Another disadvantage of using a cuff is that the nerve trunk locations which may be practically accessed surgically to implant the cuff often include nerve branches going to the retrusor muscles, which when activated may move the tongue in the wrong direction closing the airway instead of opening.

Furthermore, stimulating at motor points 54A, 54B, 55A, and/or 55B, such as at the bifurcation point of a motor neuron attaching to muscle fibers, may provide advantages such as for better control of muscle movement. Because motor points 54A, 54B, 55A, and 55B are spatially distributed, by stimulating motor points 54A, 54B, 55A, and/or 55B, the amount of the genioglossus and geniohyoid muscle being stimulated may be controlled. Also, stimulating at motor points 54A, 54B, 55A, and/or 55B may allow for more gentle muscle activation. For instance, when stimulation is provided near the trunk of hypoglossal nerve 11 or both motor points 54A and 54B and/or motor points 55A and 55B, even stimulation signal with relatively small amplitude may cause the genioglossus and/or geniohyoid muscle to fully protrude, e.g., there is high loop gain where small stimulation amplitudes cause large muscle protrusion. Fine tuning of how much to protrude the genioglossus and/or geniohyoid muscle may not be available when stimulating at a trunk of hypoglossal nerve 11 or both motor points 54A and 54B and/or motor points 55A and 55B. However, there may be lower loop gain stimulating at motor points 54A, 54B, 55A, and/or 55B. For instance, a stimulation signal having a lower amplitude may move causing the genioglossus and/or geniohyoid muscle to protrude a small amount, and a stimulation signal having a higher amplitude may move causing the genioglossus and/or geniohyoid muscle to protrude a higher amount when stimulating at motor points 54A, 54B, 55A and/or 55B.

The following are example locations of motor points 54A, 54B, 55A, and 55B relative to the midline (x-axis), posterior symphysis 51 (y-axis), and depth (z-axis), where the depth is from the plane formed by the inferior border of symphysis 51 and anterior border of hyoid bone 52.

Motor points 54A may be for the right genioglossus muscle and may be located at 13.48 mm±3.59 from the x-axis, 31.01 mm±6.96 from the y-axis, and 22.58 mm±3.74 from the z-axis. Motor points 55A may be for the right geniohyoid muscle and may be located at 11.74 mm±3.05 from the x-axis, 41.81 mm±6.44 from the y-axis, and 16.29 mm±3.40 from the z-axis. Motor points 54B may be for the left genioglossus muscle and may be located at 9.96 mm±2.24 from the x-axis, 29.62 mm±9.25 from the y-axis, and 21.11 mm±4.10 from the z-axis. Motor points 55B may be for the left geniohyoid muscle and may be located at 11.45 mm±1.65 from the x-axis, 39.63 mm±8.03 from the y-axis, and 15.09 mm±2.41 from the z-axis.

FIGS. 4A and 4B are conceptual diagrams respectively illustrating example electrical leads 20A and 20B (collectively, "electrical leads 20") that may be used for stimulation of the phrenic nerve in delivering CSA therapy. As illustrated in FIGS. 4A and 4B, electrical leads 20A and 20B may respectively have electrodes 130A, 130B, and 130C, and electrodes 130D and 130E (collectively, "electrodes 130") along respective distal portions 25A and 25B (collectively, "distal portions 25"). Distal portions 25 of leads 20 are configured to be implanted intravascularly proximate to phrenic nerve(s) 27 within the patient 14. Electrical lead 20A may have fixation mechanism 135 along the length of lead body 22 or another fixation mechanism (not shown) near electrode 130A. Electrode 130D of electrical lead 20B has a helical configuration which may be used for fixation. Other fixation mechanisms may include fixation screws capable of retracting into and extending from lead body 22. This type of mechanism may be retracted when lead 20 is passed through the vasculature to avoid unintended interactions between the mechanism and patient tissue. Another example fixation configuration may be any mechanical configuration used to increase the outside diameter of the lead to wedge the lead into place.

In general, leads 20 are described as being delivered vascularly to a position proximate to the phrenic nerve. In some examples, however, a lead 20 configured to stimulate the phrenic nerve may be placed near the phrenic nerve by percutaneous methods, e.g., similar to lead 21 discussed above.

In some examples, electrodes 130 may be used as unipolar electrodes to provide stimulation and/or for sensing in connection with an electrode (e.g., housing 15) on IMD 16. In some examples, two or more of electrodes 130 may be used together, e.g., as bipolar electrodes, each of electrodes 130 providing stimulation and/or sensing electrical signals in connection with another electrode 130 on a lead 20. In the example illustrated by FIG. 4A, electrodes 130B and 130C may provide a relatively more closely spaced bipolar pair of electrodes as compared to either of electrodes 130B and 130C with electrode 130A, which may be used for delivery of electrical stimulation to the phrenic nerve and/or sensing electrical signals. In some examples, leads 20 may include more electrodes 130, fewer electrodes 130, or different arrangements of electrodes 130 on leads 20.

In some examples, IMD 16 senses electrical signal via electrodes 130, electrodes 30, one or more electrodes on housing 15, and/or other electrodes. For example, IMD 16 may electrical signals attendant to the depolarization and repolarization of the heart, e.g., a cardiac electrogram (EGM) or electrocardiogram (ECG). As another example, IMD 16 may sense a bioimpedance or other impedance, such as a thoracic impedance or impedance of tissue proximate to a pair of electrodes. In some examples, IMD 16 may be configured to sense various signals attendant to the activation of diaphragm 90 (FIG. 1) in response to electrical stimulation to phrenic nerve(s) 27. IMD 16 may also include or be coupled to other sensors, such as one or more accelerometers for detecting other physiological parameters of a patient, such as activity or posture.

Electrical lead 20 may include one or more fixation mechanisms, e.g., active and/or passive, to provide stability of the locations of electrodes 130, e.g., for stimulation of phrenic nerve(s) 27. In the illustrated examples, leads 20 includes active fixation mechanisms 130D and 135 provided at distal portions 25 of leads 20. Active fixation mechanisms 130D and 135 and/or leads 20 may be rotated when electrodes 130 are located at a desired position to cause the active fixation mechanisms to pierce and become fixedly engaged with adjacent tissue, substantially precluding further movement of leads 20 and/or electrodes 130.

Techniques for stimulating one or more of phrenic nerve(s) 27 are primarily described herein as being performed by IMD 16, e.g., by a processing circuitry 57 (FIG. 5) of IMD 16. For example, IMD 16 may process respiratory-based signals to determine whether the IMD 16 should continue to deliver phrenic nerve stimulation based on current parameters, or whether adjustments to the parameters should be made. Processing circuitry 57 in IMD 16 may also control which of OSA and CSA therapy IMD 16 delivers at any given time, and the parameters used by IMD 16 to deliver therapy.

FIG. 5 is block diagram illustrating example configurations of implantable medical devices (IMDs) which may be utilized in the system of FIG. 1. As shown in FIG. 5, IMD 16 includes sensing circuitry 56, processing circuitry 57, therapy delivery circuitry 58, switch circuitry 59, memory 60, telemetry circuitry 61, and power source 62. IMD 16 may include a greater or fewer number of components. IMD 16 may be used for chronic stimulation, but an external medical device may also be used for trialing, which may be similar to IMD 16, but need not necessarily be similar to IMD 16.

In the illustrated examples, IMD 16 is coupled to a plurality of electrodes 230A-230N (collectively, "electrodes 230"). Electrodes 230 may include electrodes 30 (FIG. 2), electrodes 130 (FIG. 4), one or more electrodes on housing 15 of IMD 16 (FIG. 1), and/or other electrodes electrically coupled to IMD 16. Switch circuitry 59 may be configured to, in response to instructions from processing circuitry 57, switch the coupling of electrodes 230 between sensing circuitry 56 and therapy delivery circuitry 58. IMD 16 may include switch circuitry 59 such as to selectively connect and disconnect electrodes 230 from therapy delivery circuitry 58, e.g., depending on which, if any of OSA and CSA therapy are delivered at a given time.

In some examples, IMD 16 may include one or more sensors configured to sense posture or position of patient 14. For example, IMD 16 may include one or more accelerometers, such as a 3-axis accelerometer 84, to determine a posture of patient 14. Accelerometer 84 may sense motion associated with respiration. Processing circuitry 57 may use a signal produced by accelerometer 84 to sense, "healthy/normal" respirations, apnea event, and features of the respiration signal by which apnea events may be classified as OSA, CSA, or mixed OSA/CSA.

Sensing circuitry 56 may also include circuitry to detect a cardiac electrical signal, such as a cardiac EGM and/or an ECG, via a selected two or more of electrodes 230. In the illustrated example, sensing circuitry 56 includes ECG sensing circuitry 82, which may be used to sense a subcutaneous ECG, as well as to detect depolarization and/or morphological features in the ECG. In addition, since the ECG signal produced by ECG sensing circuitry 82 may vary based on respiration of the patient, ECG sensing circuitry 82 may be used to detect respiration, including apnea events and features of a respiration signal by which apnea events may be classified as "healthy/normal", OSA, CSA, or mixed OSA/CSA.

Sensing circuitry 56 may also include impedance sensing circuitry 86 configured to measure impedance using two or more of electrodes 230. Impedance sensing circuitry 86 may detect thoracic impedance and/or tissue impedance, as examples. Since such impedances may vary based on patient respiration, impedance sensing circuitry 86 may also be used to detect respiration, including apnea events and features of a respiration signal by which apnea events may be classified as "healthy/normal", OSA, CSA, or mixed OSA/CSA.

Sensing circuitry 56 may include a variety of additional or alternative circuitry for sensing a respiration signal, or other signals indicative of apnea or useful for distinguishing between "healthy/normal", OSA, CSA, and mixed OSA/CSA respiration. For example, movement sensed by accelerometer 84 or another motion sensor may indicate if patient 14 is having restless sleep, which may be indicative of the onset of OSA. As another example, sensing circuitry 56 may include acoustical sensors or a microphone for detecting vibrations in upper airway 48. Vibrations in upper airway 48 may be indicative of the onset of OSA. In some examples, sensing circuitry 56 may be configured to sense electromyogram (EMG) signals via two or more of electrodes 230. Sensing circuitry 56 may be switchably coupled to electrodes 230, e.g., electrodes 30 of FIG. 1, via switch circuitry 59 to be used as EMG sensing electrodes when electrodes 230 are not being used for stimulation. Processing circuitry 57 may use EMG signals to detect sleep state and/or low tonal state of protrusor muscles 42 and/or 46 for use in detecting OSA and delivering electrical stimulation configured to treat OSA.

Sensing circuitry 56 may include any of a variety of components for sensing any of the signals described herein. For example, sensing circuitry 56 may include amplifiers, filters, sample and hold circuitry, and/or other circuitry configured to condition a signal and sense features of the signal. In some examples, sensing circuitry 56 may include analog-to-digital conversion circuitry to provide digitized versions of signals to processing circuitry 57 for analysis, e.g., as described herein.

In general, IMD 16 may comprise any suitable arrangement of hardware, alone or in combination with software and/or firmware, to perform the techniques attributed to IMD 16 and processing circuitry 57, therapy delivery circuitry 58, and telemetry circuitry 61 of IMD 16. In various examples, IMD 16, e.g., processing circuitry 57, may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 16 also, in various examples, may include a memory 60, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although sensing circuitry 56, processing circuitry 57, therapy delivery circuitry 58, switch circuitry 59, and telemetry circuitry 61 are described as separate circuitry, in some examples, sensing circuitry 56, processing circuitry 57, therapy delivery circuitry 58, switch circuitry 59, and telemetry circuitry 61 are functionally integrated. In some examples, sensing circuitry 55, processing circuitry 57, therapy delivery circuitry 58, switch circuitry 59, and telemetry circuitry 61 correspond to individual hardware units, such as ASICs, DSPs, FPGAs, or other hardware units.

Memory 60 stores therapy programs 63 specifying stimulation parameter values for the electrical stimulation provided by IMD 16. Memory 60 may also store instructions for execution by processing circuitry 57, in addition to stimulation programs 63. For example, memory 60 may store various instructions, as well as thresholds or other parameters, used by processing circuitry 57 for sensing respiration and apnea events, and distinguishing between "healthy/normal", OSA, CSA, and OSA/CSA. Information related to sensed parameters of patient 14, e.g., from sensing circuitry 56 or the one or more sensors of IMD 16, may be recorded for long-term storage and retrieval by a user, and/or used by processing circuitry 57 for adjustment of stimulation parameters, e.g., amplitude, pulse width, and pulse rate. In some examples, memory 60 includes separate memories for storing instructions, electrical signal information, and stimulation programs 62. In some examples, processing circuitry 57 may select new stimulation parameters for a stimulation program 62 or new stimulation program from stimulation programs 62 to use in the delivery of the electrical stimulation based on patient input and/or monitored physiological states after termination of the electrical stimulation.

Generally, therapy delivery circuitry 58 generates and delivers electrical stimulation under the control of processing circuitry 57. In some examples, processing circuitry 57 controls therapy delivery circuitry 58 by accessing memory 60 to selectively access and load at least one of stimulation programs 62 to therapy delivery circuitry 58. For example, in operation, processing circuitry 57 may access memory 60 to load one of stimulation programs 62 to therapy delivery circuitry 52.

By way of example, processing circuitry 57 may access memory 60 to load one of stimulation programs 62 to therapy delivery circuitry 58 for delivering the electrical stimulation to patient 14. A clinician or patient 14 may select a particular one of stimulation programs 62 from a list using a programming device, such as a patient programmer or a clinician programmer. Processing circuitry 57 may receive the selection via telemetry circuitry 61. Therapy delivery circuitry 58 delivers the electrical stimulation to patient 14 according to the selected program for an extended period of time, such as minutes or hours while patient 14 is asleep, e.g., as determined from the one or more sensors and/or sensing circuitry 56. For example, processing circuitry 57 may control switch circuitry 59 to couple electrodes 30 to therapy delivery circuitry 58.

Therapy delivery circuitry 58 delivers electrical stimulation according to stimulation parameters. In some examples, therapy delivery circuitry 58 delivers electrical stimulation in the form of electrical pulses. In such examples, relevant stimulation parameters may include a voltage amplitude, a current amplitude, a pulse rate, a pulse width, a duty cycle, or the combination of electrodes 30 therapy delivery circuitry 58 uses to deliver the stimulation signal. In some examples, therapy delivery circuitry 58 delivers electrical stimulation in the form of continuous waveforms. In such examples, relevant stimulation parameters may include a voltage or current amplitude, a frequency, a shape of the stimulation signal, a duty cycle of the stimulation signal, or the combination of electrodes 30 therapy delivery circuitry 58 uses to deliver the stimulation signal.

In some examples, the stimulation parameters for the stimulation programs 62 may be selected to cause protrusor muscles 42 and/or 46 to a protruded state, e.g., to open-up airway 48. An example range of stimulation parameters for the electrical stimulation likely to be effective in treating OSA, e.g., upon application to hypoglossal nerves 11 or both motor points 54A and 54B and/or motor points 55A and 55B, are as follows:

1. Frequency or pulse rate: between about 30 Hz and about 50 Hz, such as about 40 Hz. In some examples, the minimum target frequency is used which may achieve muscle tetany, e.g., constant contraction, and the provide the required force to open the airway.
2. Amplitude: between about 0.5 milliamps (mA) and about 3 mA, with average of approximately 1.5 mA. The maximum amplitude may be approximately 10 mA. In some examples, bilateral stimulation may be delivered with the same or different amplitudes for the left and right sides of the patient, such as 1.3 mA for the left side, and 1.5 mA for the right side.
3. Pulse Width: between about 100 microseconds (μs) and about 500 μs. In some examples, a pulse width of 150 μs might be used for minimal power consumption. In some examples, the pulse width is 210 μs. In some cases, shorter pulse widths may result in higher current or voltage amplitudes. In yet other cases, pulse shape waveform variations such as rectangle, sawtooth, triangle, monophasic, biphasic, etc. and/or any technique to manipulate the electrical field to vary recruitment of nerve fibers.

In some examples, higher amplitudes or longer pulse duration may increase movement of tongue 40 by recruiting additional motor units. A pulse width of typically 200 μs evokes most large and small muscle fiber/motor units for near-maximal effect. Shorter pulse widths such as less than or equal 200 μs may recruit the largest most fatigue-resistant muscle fibers. Long-pulse duration such as greater than 200 μs may recruit large motor fibers and the smallest fast fatiguing muscle fibers. Titrating the pulse width duration may be used to minimize recruitment fatigue sustaining maximal clinical movement effect over the treatment period.

Processing circuitry 57 may select therapy programs 63 for alternating delivery of electrical stimulation between stimulating left protrusor muscles 42 and/or 46 and right protrusor muscles 42 and/or 46, such as in examples where two leads 20 are implanted. In some examples, there may be some overlap in the delivery of electrical stimulation so for some of amount of time both left and right protrusor muscles 42 and/or 46 are being stimulated. In some examples, there may be a pause in alternating stimulation (e.g., stimulate left protrusor muscles, a time period with no stimulation, then stimulate right protrusor muscles, and so forth). Processing circuitry 50 may also select stimulation programs 62 selecting between different combinations of electrodes 30 for stimulating, such as to stimulate different locations of hypoglossal nerve(s) 11 or both motor points 54A and 54B and/or motor points 55A and 55B, which may help with fatigue as well as provide more granular control of how much to protrude tongue 40.

In some examples, therapy delivery circuitry 58 drives electrodes 30 of lead 21 for treatment of OSA, and electrodes 130, 130A of lead 20 for treatment of CSA. Specifically, therapy delivery circuitry 58 may deliver electrical stimulation to tissue of patient 14 via selected electrodes 30 carried by lead 21 and selected electrodes 130, 130A carried by lead 20. The electrical stimulation delivered via electrodes 130 to treat CSA may be, in at least some aspects similar to cardiac pacing, and may be referred to as phrenic pacing. Example parameters for CSA stimulation may be as follows:

Frequency or pulse rate: between about 10 Hz and 100 Hz, such as about 60 Hz.

Amplitude: between about 0 mA and 10 mA, such as about 8.1 mA. Stimulation amplitude may be varied in a sinusoidal pattern, e.g., corresponding to a normal respiration rate for an adult at rest of 12 to 20 breaths per minute. Typically, the inhalation/exhalation ratio is 1:2, i.e., twice the amount of time in the exhalation phase than the inhalation phase. With such a ration, a four second breath cycle (15 breaths per min) will break down to 1.33 seconds of inspiration and 2.66 second of expiration. In some examples, stimulation is only applied during inspiration in a ramping pattern to produce a smooth diaphragm contraction. During expiration the stimulation may be turned off and the diaphragm 90 relaxes.

Pulse Width: between about 60 microseconds (usec) and 1,000 usec, such as about 500 usec.

In some examples, processing circuitry 57 may control therapy delivery circuitry 58 to deliver or terminate the electrical stimulation based on patient input received via telemetry circuitry 61. Telemetry circuitry 61 includes any suitable hardware, firmware, software or any combination thereof for communicating with another device, such as an external device. Under the control of processing circuitry 57, telemetry circuitry 61 may receive downlink telemetry, e.g., patient input, from and send uplink telemetry, e.g., an alert, to a programmer with the aid of an antenna, which may be internal and/or external. Processing circuitry 57 may provide the data to be uplinked to the programmer and the control signals for telemetry circuitry 61 and receive data from telemetry circuitry 61.

Generally, processing circuitry 57 controls telemetry circuitry 61 to exchange information with a medical device programmer and/or another device external to IMD 16. Processing circuitry 57 may transmit operational information and receive stimulation programs or stimulation parameter adjustments via telemetry circuitry 61. Also, in some examples, IMD 16 may communicate with other implanted devices, such as stimulators, control devices, or sensors, via telemetry circuitry 61.

Power source 62 delivers operating power to the components of IMD 16. Power source 62 may include a battery and a power generation circuit to produce the operating power. In some examples, the battery may be rechargeable to allow extended operation. Recharging may be accomplished through proximal inductive interaction between an external charger and an inductive charging coil within IMD 16. In other examples, an external inductive power supply may transcutaneously power IMD 16 whenever electrical stimulation is to occur.

Figure 6:
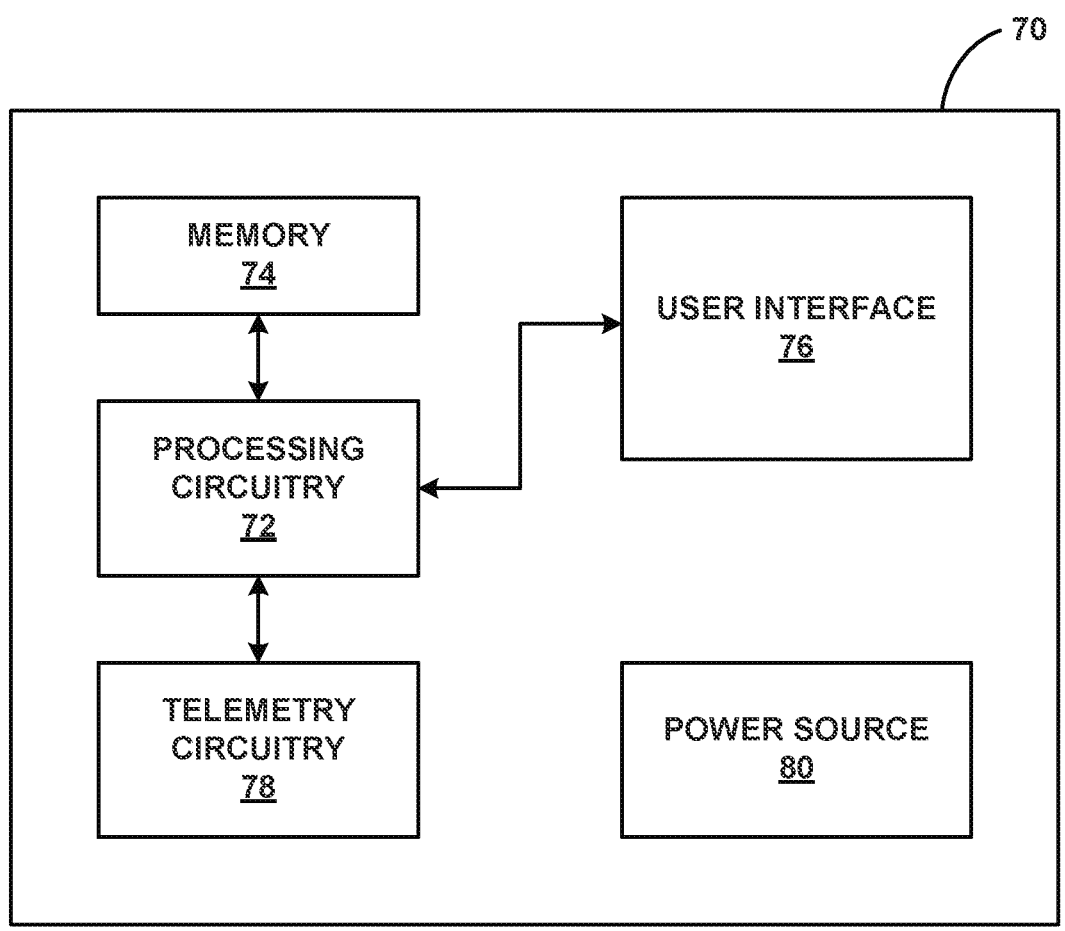
FIG. 6 is a block diagram illustrating an example configuration of an external device according to one or more examples.

FIG. 6 is a block diagram illustrating an example configuration of an external device 70. While external device 70 may generally be described as a hand-held computing device, the external device may be a notebook computer, a cell phone, or a workstation, for example. As illustrated in FIG. 6, external device 70 may include processing circuitry 72, memory 74, user interface 76, telemetry circuitry 78, and power source 80.

In general, external device 70 comprises any suitable arrangement of hardware, alone or in combination with software and/or firmware, to perform the techniques attributed to external device 70, and processing circuitry 72, user interface 76, and telemetry module 78 of external device 70. Examples of processing circuitry 72 may include one or more processors, such as one or more microprocessors, DSPs, ASICs, FPGAs, or any other equivalent integrated or discrete logic circuitry, as well as any combinations of such components. Examples of memory 74 include RAM, ROM, PROM, EPROM, EEPROM, flash memory, a hard disk, a CD-ROM, comprising executable instructions for causing the one or more processors to perform the actions attributed to them. Moreover, although processing circuitry 72 and telemetry circuitry 78 are described as separate circuitry, in some examples, processing circuitry 72 and telemetry circuitry 78 are functionally integrated. In some examples, processing circuitry 72 and telemetry circuitry 78 correspond to individual hardware units, such as ASICs, DSPs, FPGAs, or other hardware units.

In some examples, memory 74 may further include program information, e.g., stimulation programs, defining the electrical stimulation, similar to those stored in memory 60 of IMD 16. The stimulation programs stored in memory 74 may be downloaded into memory 60 of IMD 16.

User interface 76 may include a button or keypad, lights, a speaker for voice commands, a display, such as a liquid crystal (LCD), light-emitting diode (LED), or cathode ray tube (CRT). In some examples the display may be a touch screen. As discussed in this disclosure, processing circuitry 72 may present and receive information relating to electrical stimulation and resulting therapeutic effects via user interface 76. For example, processing circuitry 72 may receive patient input via user interface 76. The input may be, for example, in the form of pressing a button on a keypad or selecting an icon from a touch screen.

Processing circuitry 72 may also present information to the patient in the form of alerts related to delivery of the electrical stimulation to patient 14 or a caregiver via user interface 76. Although not shown, external device 70 may additionally or alternatively include a data or network interface to another computing device, to facilitate communication with the other device, and presentation of information relating to the electrical stimulation and therapeutic effects after termination of the electrical stimulation via the other device.

Telemetry circuitry 78 supports wireless communication between IMD 16 and external device 70 under the control of processing circuitry 72. Telemetry circuitry 78 may also be configured to communicate with another computing device via wireless communication techniques, or direct communication through a wired connection. In some examples, telemetry circuitry 78 may be substantially similar to telemetry circuitry 61 of IMD 16 described above, providing wireless communication via an RF or proximal inductive medium. In some examples, telemetry circuitry 61 may include an antenna, which may take on a variety of forms, such as an internal or external antenna.

Examples of local wireless communication techniques employed to facilitate communication between programmer 70 and another computing device include RF communication according to the 802.11 or Bluetooth specification sets, infrared communication, e.g., according to the IrDA standard, or other standard or proprietary telemetry protocols. In this manner, other external devices may be capable of communicating with external device 70 without needing to establish a secure wireless connection. Power source 80 delivers operating power to the components of external device 70. Power source 80 may include a battery and a power generation circuit to produce the operating power. In some examples, the battery may be rechargeable to allow extended operation.

It should be noted system 10, and the techniques described herein, may not be limited to treatment or monitoring of a human patient. In alternative examples, system 10 may be implemented in non-human patients, e.g., primates, canines, equines, pigs, and felines. These other animals may undergo clinical or research therapies benefiting from the subject matter of this disclosure. Various examples are described herein, such as the following examples.

In an example of techniques disclosed, a system 10 may have a first lead 21, which may have a first plurality of electrodes 30. System 10 may have a second lead 20, which may have a second plurality of electrodes 130, 130A. Therapy delivery circuitry 58 may be coupled to the first and second leads 21, 20. Therapy delivery circuitry 58 may deliver a first electrical stimulation via the first lead 21. The first electrical stimulation may treat obstructive sleep apnea. A second electrical stimulation via the second lead 20 may treat central sleep apnea. Sensing circuitry 56 may sense one or more signals, where each of the one or more signals include respirations. Processing circuitry 57 may detect apneas based on timing of the respirations. Processing circuitry 57 may characterize the apneas as one of obstructive sleep apnea, central sleep apnea, or mixed sleep apnea based on at least one of a frequency spectrum or a morphology of the respirations. In some examples, processing circuitry 57 may also be configured to provide a "normal/healthy" characterization based on at least one of a frequency spectrum or a morphology of the respirations, and/or determine that no characterization can be made with sufficient confidence, e.g., an "unknown" characterization. Based on the characterization, processing circuitry 57 may control the therapy delivery circuitry 58 to deliver one of the first electrical stimulation, the second electrical stimulation, both the first and second electrical stimulation in combination, or no stimulation.

Figure 7:
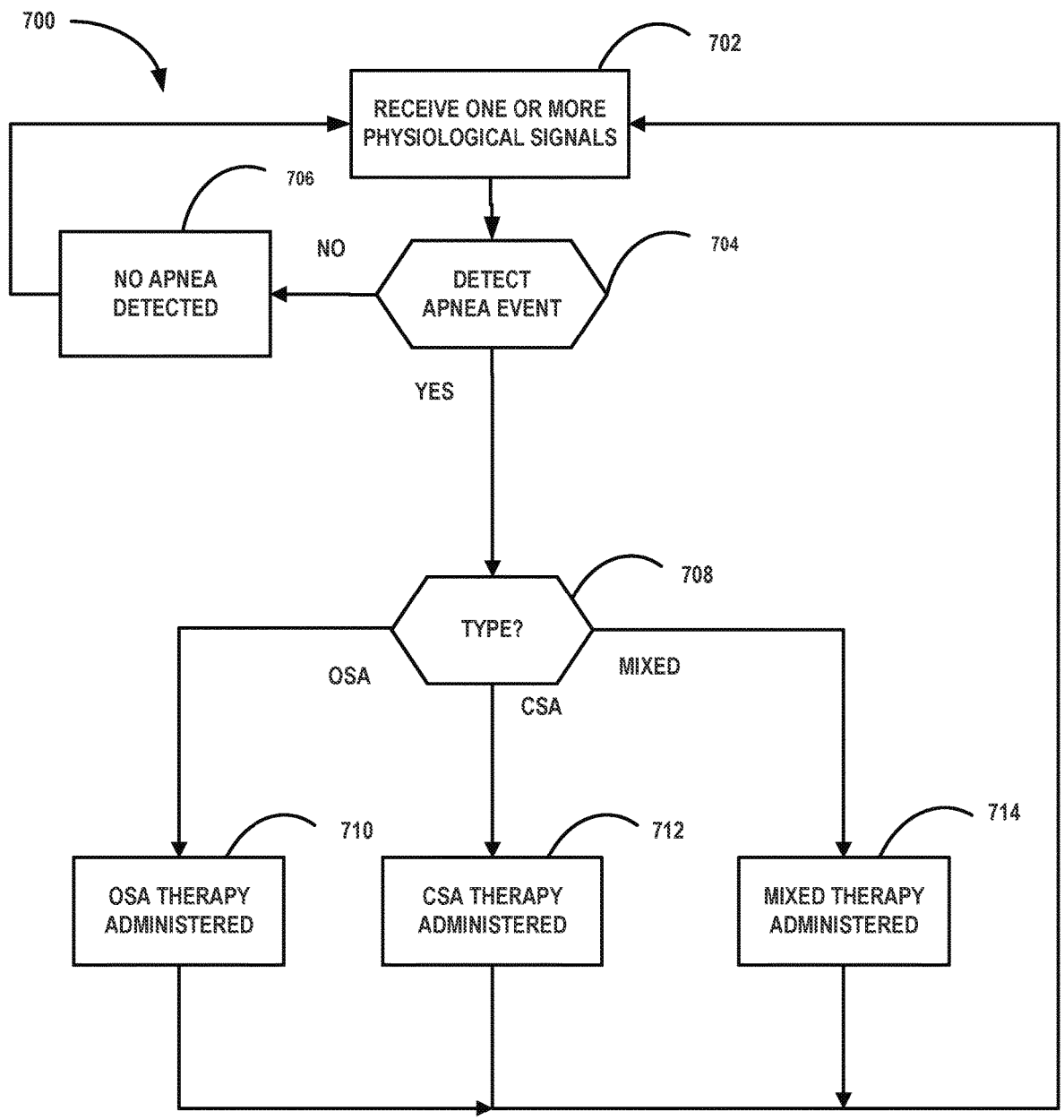
FIG. 7 is a flow diagram of an example method for detecting and treating OSA, CSA, and combination OSA/CSA according to one or more examples.
Figure 8A:
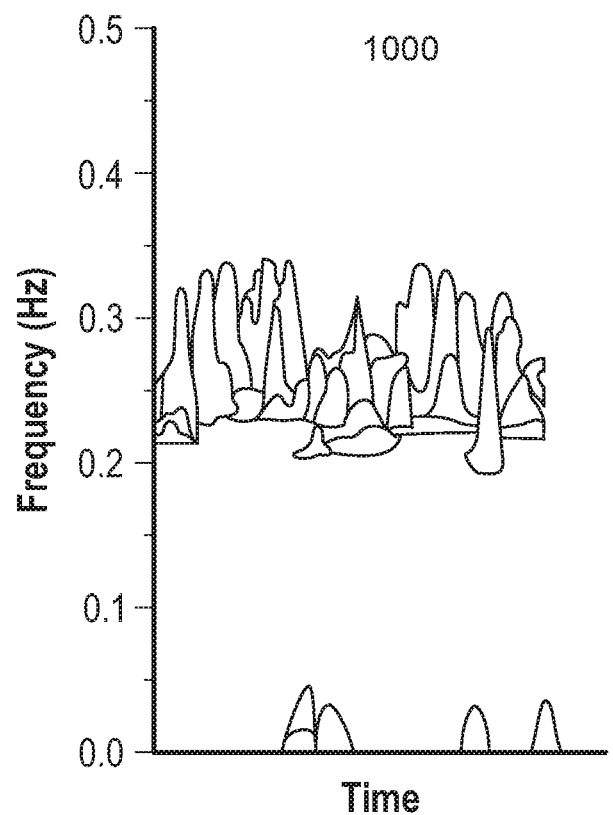
FIGS. 8A, 8B, 8C and 8D are graphical diagrams of sleep spectrograms according to one or more examples.
Figure 8B:
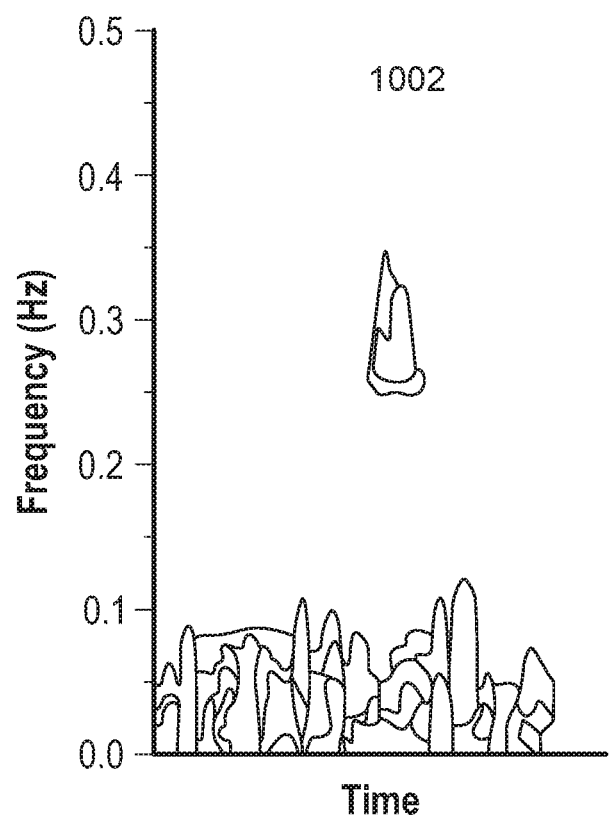
Figure 8C:
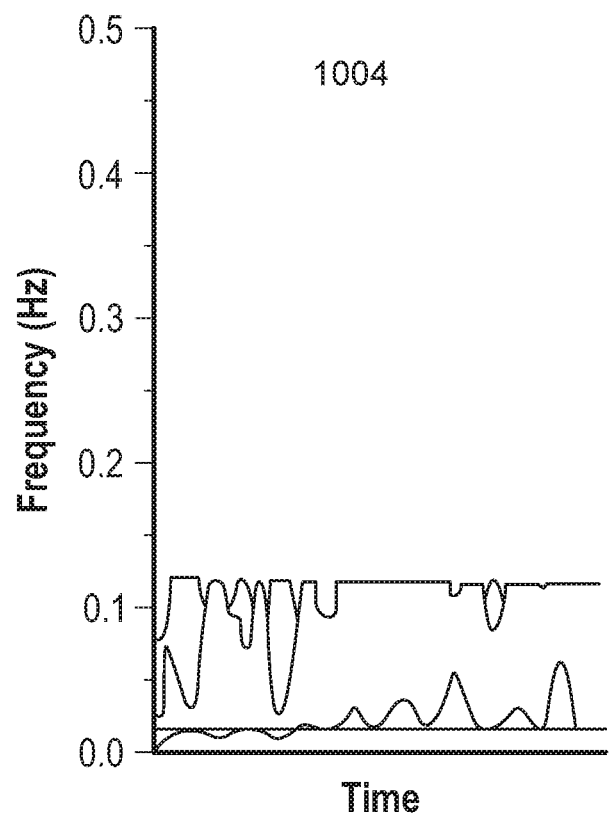
Figure 8D:
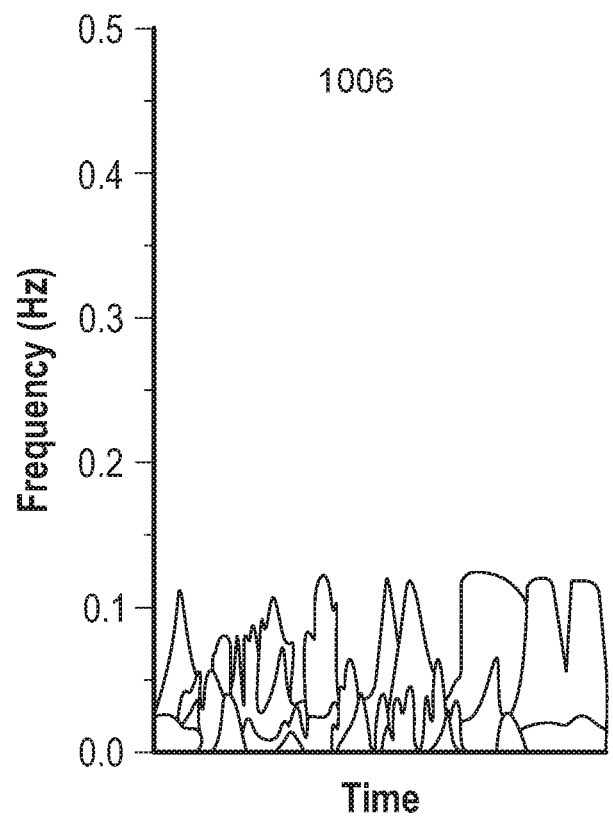

FIG. 7 is a flow diagram of an example method 700, e.g., including an auto-sensing feedback loop, for detecting and treating OSA, CSA and combination OSA/CSA. Method 700 may be a program stored in memory 60 and may be a therapy program stored within therapy programs 63. Processing circuitry 57 may execute method 700.

Although described in the context of an example in which IMD 16 performs the example method 700 of FIG. 7, in other examples, external device 70 may perform at least some of the example method of FIG. 7. In some examples, external device 70 may receive one or more physiological signals or parameters derived from such signals, e.g., from IMD 16 or one or more other implanted or external devices, and determine whether to deliver one or more electrical stimulation therapies according to the example of FIG. 7.

In an example, processing circuitry 57 may receive one or more physiological signals, e.g., sensed by sensing circuitry 56 (702). Each of the one or more physiological signals may include respirations of patient 14. Processing circuitry 57 may detect apnea events based on a primary biomarker in the one or more physiological signals (704). A primary biomarker may be any physiological signal indicating an apnea event. The physiological signal may come from accelerator 84, ECG sensor 82 and/or bio-impedance sensor 86. In some examples, processing circuitry 57 may detect respirations in such signals based on an amplitude of the signals, an amplitude of a derivative of the signals, and/or an area under the curve of the signals satisfying one or more thresholds, which may be fixed or variable over time. In some examples, the primary biomarker for apnea detection is respiration, and processing circuitry 57 may detect apnea based on an absence of respiration for a threshold period of time and/or based on morphological feature of the respiration signals.

If no apnea is detected (NO branch of 704), no therapy stimulation is necessary (706), therapy delivery circuitry 58 remains in an "OFF" condition or powered down, thus conserving power source 62.

If an apnea event is detected (YES branch of 704), processing circuitry 57 characterizes each of the apnea events as one of an OSA event, a CSA event, or a combination OSA/CSA event based on a secondary biomarker (discussed in greater detail below) in the one or more physiological signals (708). Therapy delivery circuitry 58 may provide a first electrical stimulation configured to treat OSA in response to a first one or more of the apnea events being characterized as OSA events (OSA branch of 708) (710). Therapy delivery circuitry 58 may provide a second electrical stimulation configured to treat CSA in response to a second one or more of apnea events being characterized as CSA events (CSA branch of 708) (712). Therapy delivery circuitry 58 may provide a third electrical stimulation configured to treat combination OSA/CSA in response to a third one or more of the apnea events being characterized as combination OSA/CSA events (MIXED branch of 708) (714). After each therapy administered, processing circuitry 57, continues to receive one or more physiological signals to detect an apnea event (702).

One of the one or more physiological signals may be an accelerometer signal, a cardiac electrogram signal and/or a bioimpedance signal. Processing circuitry 57 may detect a primary biomarker indicating an OSA, CSA or a combination OSA/CSA event (704). Respiration may be used as the primary biomarker, and may be discriminated with any combination of accelerometer 84, ECG sensor 82, or bio-impedance sensor 86. Example method 700 may have greater sensitivity and specificity, the more sensors which are integrated into a respiration sensing algorithm. As discussed above, IMD 16 provides accelerometer 84, ECG sensor 82, or bio-impedance sensor 86 which may be used to quantitatively and qualitatively measure the patient's respiration.

In some examples, 3-axis accelerometer sensor 84 may be used for respiration detection. While 3-axis accelerometers may be very accurate, they may draw relatively high current and, consequently, may necessitate infrequent sampling. Thus, 3-axis accelerometer 84 may not be relied upon continuously, in some examples.

ECG sensing circuitry 82 may also be used for respiration detection. An ECG vector may be taken from CSA lead tip 130A to IMD housing 15, which may be used as an electrode. Another subcutaneous ECG vector may be taken from two embedded ECG electrodes located on IMD housing 15, discussed above. ECG sensing is a low-current draw and allows for frequent sampling. However, ECG sensing is also susceptible to noise from within the body (e.g., heart beating, brain activity, etc.).

Bio-impedance sensor 86 may also be used for respiration detection. A vector from CSA lead tip 130A to IMD housing 15 may be useful for detecting respiration based on bio-impedance. Bio-impedance sensing is a moderate-current draw, which allows for sampling frequency less than ECG sensor 82 but more than accelerometer sensor 84. Bio-impedance fidelity increases with vector distance, hence CSA lead tip 130A to IMD housing 15 may have more signal fidelity than two embedded ECG electrodes located on IMD 16.

The primary biomarker may be an ECG derived respiration, an impedance derived respiration, or an accelerometer derived respiration, or a respiration derived from any combination of these signals. Anyone of the primary biomarkers may provide enough information to detect an apnea event (704).

In the example method of FIG. 7, processing circuitry 57 detects one or more apnea events, and responsively characterizes the respiration as one of OSA, CSA, or mixed OSA/CSA. In other examples, there may be more of less classifications or characterizations that can be made by processing circuitry 57.

In some examples, processing circuitry 57 may additionally or alternatively be configured to classify or characterize respiration as "healthy/normal," e.g., in response to detecting one or more apnea events. Healthy/normal respiration may be used as a "safety" comparison when determining OSA, CSA, or MIXED apnea event, e.g., to avoid delivery of stimulation where apneas were misidentified using the primary biomarker or were correctly identified but were of a transient nature. Processing circuitry 57 may determine that respiration should be classified as healthy/normal based on the secondary biomarker as described herein, e.g., based on one or both of a frequency or morphology of one or more respiration signals. Healthy/normal respiration may be determined as another type of respiration (708). In response to classifying the respiration as healthy/normal, processing circuitry 57 may control therapy delivery circuitry 58 to suspend or stop delivery of a therapy, e.g., a therapy configured to treat one or both of OSA and CSA.

In some examples, processing circuitry 57 may additionally be configured to determine that respiration cannot be classified (708) in response to detecting one or more apneas (704), e.g., because none of the criteria associated with other classifications, such as OSA, CSA, mixed OSA/CSA, and/or healthy/normal, are satisfied by the one or more physiological signals indicative of respiration. In response to being unable to determine one of the classifications, processing circuitry 57 may control therapy delivery circuitry 58 to deliver a default or "safety mode" therapy. The default or safety mode therapy could be selectable by a user and/or could default to the therapy configured to treat mixed OSA/CSA.

In some examples, the classification of a type of respiration based on a secondary biomarker, e.g., 708 of FIG. 7, may include a series of sequential determinations of whether the respiration signal(s) satisfy criteria for different classifications. For example, if processing circuitry 57 determines that OSA detected (708), processing circuitry 57 may control therapy delivery circuitry 58 deliver OSA therapy (710). If OSA is not detected (708), processing circuitry 57 may determine whether CSA is detected (708). If CSA is detected, processing circuitry 57 may control therapy delivery circuitry 58 to deliver therapy configured to treat CSA (712). If CSA is not detected, processing circuitry 57 may determine whether one or more criteria to classify respiration as mixed OSA/CSA are satisfied (708) and, if so, deliver both OSA+CSA therapy (714).

If the criteria for mixed OSA/CSA are not satisfied, processing circuitry 57 may determine whether one or more criteria for "healthy/normal" respiration are satisfied. If the criteria for healthy/normal respiration are satisfied, processing circuitry 57 may control therapy delivery circuitry 58 to turn therapy off (706). In some examples, e.g., if processing circuitry 57 is unable to determine any of the classifications, IMD 16 may default to a "safety mode" therapy delivery (e.g., could be selectable, but default to mixed therapy delivery). In examples of the present disclosure, if "healthy/normal" detection inconclusive, processing circuitry 57 may default to a "safety mode" therapy delivery (e.g., where mixed therapy delivery may be used as default; or a programmable selection for OSA therapy, CSA therapy, or MIXED therapy or a no therapy over-ride).

FIGS. 8A, 8B, 8C and 8D are a graphical diagram of a sleep spectrogram according to one or more examples. OSA and CSA have different physiologic origins, which may be better detected through the creation of a "sleep spectrogram" by morphing several different physiological signals together by processing circuitry 57. In OSA, the upper airway becomes partially or completely blocked while patient 14 sleeps. In CSA, there is cessation of respiratory drive resulting in a lack of respiratory movements (e.g., a lack of lower brain stem signal). In mixed OSA/CSA there is a parallel blending of the primary biomarkers.

Processing circuitry 57 may combine the three primary respiration sensor signals to create a "sleep spectrogram," which may provide increased sensitivity and specificity to discriminate between OSA, CSA, or mixed OSA/CSA manifestations and allow automatic and appropriate therapy delivery.

Sleep spectrogram 1000 shows a "healthy/normal" sleep spectrogram, for which no therapy may be needed and patient 14 may be sleeping well. In examples of the present disclosure, "healthy/normal" respiration may be used as a "safety" comparison or reference point when determining OSA, CSA or mixed OSA/CSA apnea event. Processing circuitry 57 may use sleep spectrogram 1000 or similar respiration signal data to determine a type of therapy. If processing circuitry 57 determines a "healthy/normal" sleep spectrogram, therapy delivery circuitry 58 remains off. From cardiopulmonary sleep spectrogram 1000, "healthy/normal" spectrogram energy is primarily 0.2 to 0.3 Hz with a predominant "spiked" morphology.

If sleep spectrogram or similar data has features similar to those of sleep spectrogram 1002, processing circuitry 57 may determine an OSA event is occurring within patient 14. From cardiopulmonary sleep spectrogram 1002, OSA spectrogram energy is primarily 0.0 to 0.1 Hz with a predominant "spiked" morphology. In response to determining that a sleep spectrogram has features like sleep spectrogram 1002, processing circuitry 57 may then provide a stimulation therapy from therapy delivery circuitry 58 to musculature of a tongue of a patient and proximate to a hypoglossal nerve or both motor points 54A and 54B and/or motor points 55A and 55B for the OSA detected event (710).

If the sleep spectrogram or similar data has features similar to sleep spectrogram 1004, processing circuitry 57 may determine that a CSA event is occurring (708). From cardiopulmonary sleep spectrogram 1004, CSA spectrogram energy is primarily 0.0 to 0.1 Hz with a predominant "plateau" or "clipped" morphology. Processing circuitry 57 may then provide stimulation therapy from the therapy delivery circuitry 58 intravascularly proximate to a phrenic nerve for the CSA detected event (712).

If the sleep spectrogram or similar data has features similar to sleep spectrogram 1006, processing circuitry 57 may determine a mixed OSA/CSA event in occurring (708). From cardiopulmonary sleep spectrogram 1006, mixed spectrogram energy is primarily 0.0 to 0.1 Hz with a combination of spikes and plateaus co-relatable to the number of OSA events (spikes) or CSA events (plateaus). Processing circuitry 57 may then provide stimulation therapy from the therapy delivery circuitry 58 to the musculature of the tongue of the patient proximate to the hypoglossal nerve or both motor points 54A and 54B and/or motor points 55A and 55B and intravascularly proximate to the phrenic nerve for the combination OSA/CSA event (714).

Processing circuitry 57 may determine whether one or more criteria for each of a plurality of classifications is satisfied by a sleep spectrogram or other arrangement of time series of data from one or more respiration signals. The features of the data compared to the criteria may be considered secondary biomarkers, and may include frequency and/or morphology features. In some examples, a criterion for classifying the data is a frequency criterion, where energy of the signal(s) in one or more spectra may be compared to each other or one or more thresholds. In some examples, a criterion for classifying the data is a morphology criterion, where morphology of the signal(s) may be compared to one or more criterion. Morphological criteria may include whether the signals are spiked or plateaued as described above. Morphological criteria may include comparing the signal data to one or more templates, or wavelet or other decompositions of the signal to one or more template decompositions or thresholds The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

The techniques described in this disclosure, including those attributed to various modules and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated, discrete logic circuitry, or other processing circuitry, as well as any combinations of such components, remote servers, remote client devices, or other devices. The term "processor" or "processing circuitry" may refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components. For example, any module described herein may include electrical circuitry configured to perform the features attributed to that particular module, such as fixed function processing circuitry, programmable processing circuitry, or combinations thereof.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that may, over time, change (e.g., in RAM or cache).

The following examples are illustrative of the techniques described herein.

Example 1. A method comprising: receiving one or more physiological signals, each of the one or more physiological signals including respirations of a patient; detecting apnea events based on a primary biomarker in the one or more physiological signals; characterizing each of the apnea events as one of a normal event, OSA (obstructive sleep apnea) event, a CSA (central sleep apnea) event, or a combination OSA/CSA event based on a secondary biomarker in the one or more physiological signals; providing a first electrical stimulation configured to treat OSA in response to a first one or more of the apnea events being characterized as OSA events; providing a second electrical stimulation configured to treat CSA in response to a second one or more of apnea events being characterized as CSA events; and providing a third electrical stimulation configured to treat combination OSA/CSA in response to a third one or more of the apnea events being characterized as combination OSA/CSA events.

Example 2. The method of claim 1, further comprising providing one of the first, the second or the third electrical stimulation as a default based on determining that the apnea events cannot be characterized as a normal event, an OSA event, CSA or combination OSA/CSA.

Example 3. The method of example 1, wherein one of the one or more physiological signals comprise an accelerometer signal.

Example 4. The method of example 1 or 3, wherein one of the one or more physiological signals comprise a cardiac electrical signal.

Example 5. The method of any of examples 1-4, wherein one of the one or more physiological signals comprise a bioimpedance signal.

Example 6. The method of any of examples 1-5, wherein the secondary biomarker comprises at least one of a frequency spectrum or a morphology of the one or more physiological signals.

Example 7. The method of any of examples 1, 5, or 6, wherein the one or more physiological signals comprise an accelerometer signal, a cardiac electrical signal, and a bioimpedance signal.

Example 8. The method of any of examples 1-7, wherein providing the first electrical stimulation configured to treat OSA comprises delivering the first electrical stimulation via a first lead implanted within musculature of a tongue of the patient, and providing the second electrical stimulation configured to treat CSA comprises delivering the second electrical stimulation via a second lead implanted intravascularly proximate to a phrenic nerve within the patient.

Example 9. The method of any of examples 1-8, wherein providing the third electrical stimulation comprises providing both the first electrical stimulation and the second electrical stimulation.

Example 10. The method of any of examples 1-9, wherein providing the first, second, and third electrical stimulations comprises delivering the first, second, and third electrical stimulations from a single implantable medical device.

Example 11. A system comprising therapy delivery circuitry configured to be coupled to a first lead comprising a first plurality of electrodes and a second lead comprising a second plurality of electrodes. The therapy circuitry is configured to: deliver a first electrical stimulation via the first lead, the first electrical stimulation configured to treat obstructive sleep apnea (OSA); and deliver a second electrical stimulation via the second lead, the second electrical stimulation configured to treat central sleep apnea (CSA). The system further comprises sensing circuitry configured to sense one or more physiological signals, each of the one or more physiological signals including respirations of a patient, and processing circuitry. The processing circuitry is configured to: detect apnea events based on timing of the respirations; determine at least one of a frequency spectrum or a morphology of the respirations based on the detection of the apnea events; characterize the apnea events as one of normal, OSA, CSA, or combination OSA/CSA events based on the at least one of the frequency spectrum or the morphology of the respirations; and based on the characterization of the apneas, control the therapy delivery circuitry to deliver one of no electrical stimulation, the first electrical stimulation, the second electrical stimulation, or both the first and second electrical stimulation in combination.

Example 12. The system of example 11, wherein the first lead is configured to be implanted within musculature of a tongue of a patient.

Example 13. The system of example 11 or 12, wherein the second lead is configured to be implanted intravascularly proximate to a phrenic nerve within the patient.

Example 14. The system of any of examples 11-13, wherein the sensing circuitry comprises an accelerometer and one of the one or more physiological signals comprise a motion signal that includes the respirations.

Example 15. The system of any of examples 11-14, wherein the one or more physiological signals comprise a cardiac electrical signal that includes the respirations.

Example 16. The system of any of examples 11-15, wherein the one or more physiological signals comprise a bioimpedance signal that includes the respirations.

Example 17. The system of any of examples 11-16, wherein the processing circuitry is configured to control the therapy delivery circuitry to be in an off state prior to the detection of the apneas.

Example 18. The system of examples 11-13, wherein the second lead is configured to be implanted percutaneously in tissue near the phrenic nerve.

Example 19. An implantable medical device configured to be coupled to a first lead comprising a first plurality of electrodes and a second lead comprising a second plurality of electrodes, the implantable medical device comprising therapy delivery circuitry configured to: deliver a first electrical stimulation via the first lead, the first electrical stimulation configured to treat obstructive sleep apnea (OSA); and deliver a second electrical stimulation via the second lead, the second electrical stimulation configured to treat central sleep apnea (CSA). The implantable medical device further comprises sensing circuitry configured sense one or more physiological signals, each of the one or more physiological signals including respirations of a patient, and processing circuitry. The processing circuitry is configured to: detect respirations in the one or more physiological signals; detect an apnea event based on the respirations detected in the one or more sensed physiological signals; characterize the apnea as one of obstructive sleep apnea (OSA), central sleep apnea (CSA), or mixed sleep apnea (OSA/CSA) based on at least one of a frequency spectrum or a morphology of the respirations; and based on the characterization of the apneas, control the therapy delivery circuitry to deliver one of the first electrical stimulation, the second electrical stimulation, or both the first and second electrical stimulation in combination.

Example 20. The implantable medical device of example 19, wherein the first plurality of electrodes is located along a distal portion of the first lead configured to be implanted within musculature of a tongue of a patient.

Example 21. The implantable medical device of example 19 or 20, wherein the second plurality of electrodes is located along a distal portion of the second lead configured to be implanted intravascularly proximate to a phrenic nerve within the patient.

Example 22. The implantable medical device of any of examples 19-21, wherein the sensing circuitry comprises an accelerometer and one of the one or more physiological signals comprise a motion signal.

Example 23. The implantable medical device of any of examples 19-22, wherein the one or more physiological signals comprise a cardiac electrical signal.

Example 24. The implantable medical device of any of examples 19-23, wherein the one or more physiological signals comprise a bioimpedance signal.

Example 25. The implantable medical device of any of examples 19-24, wherein the processing circuitry is configured to turn off the therapy delivery circuitry when the processing circuitry does not detect an apnea event.

Various examples have been described herein. Any combination of the described operations or functions is contemplated. These and other examples are within the scope of the following claims.

What is claimed is:

1. A method comprising:
   receiving one or more physiological signals;
   detecting an apnea event based on the one or more physiological signals;
   determining that the apnea event cannot be characterized as one of a normal, OSA (obstructive sleep apnea), CSA (central sleep apnea), or combination OSA/CSA event; and
   outputting an electrical stimulation as a default based on determining that the apnea event cannot be characterized as a normal event, an OSA event, a CSA event, or combination OSA/CSA events.

2. The method of claim 1, wherein one of the one or more physiological signals comprise an accelerometer signal.

3. The method of claim 1, wherein one of the one or more physiological signals comprise a cardiac electrical signal.

4. The method of claim 1, wherein one of the one or more physiological signals comprise a bioimpedance signal.

5. The method of claim 1, wherein the one or more physiological signals comprise an accelerometer signal, a cardiac electrical signal, and a bioimpedance signal.

6. A system comprising:
   therapy delivery circuitry configured to deliver electrical stimulation;
   sensing circuitry configured to sense one or more physiological signals; and
   processing circuitry configured to:
     detect an apnea event based on the one or more physiological signals;
     determine that the apnea event cannot be characterized as one of a normal, OSA (obstructive sleep apnea), CSA (central sleep apnea), or combination OSA/CSA event; and
     control the therapy delivery circuitry to deliver a particular electrical stimulation as a default based on the determination that the apnea event cannot be characterized as a normal event, an OSA event, a CSA event, or combination OSA/CSA events.

7. The system of claim 6, wherein the therapy delivery circuitry is configured to be coupled to a first lead comprising a first plurality of electrodes and a second lead comprising a second plurality of electrodes and configured to deliver the particular electrical stimulation via one or more of the first lead or the second lead.

8. The system of claim 7, wherein the therapy delivery circuitry is configured to deliver the particular electrical stimulation via the first lead and the second lead.

9. The system of claim 6, wherein the sensing circuitry comprises an accelerometer and one of the one or more physiological signals comprise a motion signal.

10. The system of claim 6, wherein the one or more physiological signals comprise one or more of a cardiac electrical signal or a bioimpedance signal.

11. The system of claim 6, wherein the processing circuitry is configured to control the therapy delivery circuitry to be in an off state prior to the detection of the apnea event.

12. The system of claim 6, further comprising an implantable medical device, wherein the implantable medical device comprises the therapy delivery circuitry, the sensing circuitry, and the processing circuitry.

13. The system of claim 6, wherein the processing circuitry is configured to determine the apnea event cannot be characterized as one of a normal event, OSA event, a CSA event, or a combination OSA/CSA event based on a frequency spectrum or a morphology of the one or more physiological signals.

14. The system of claim 6, wherein the one or more physiological signals include one or more biomarkers,
  wherein to detect the apnea event, the processing circuitry is configured to detect the apnea event from at least one of the one or more biomarkers, and
  wherein to determine the apnea event cannot be characterized as one of a normal event, OSA event, a CSA event, or a combination OSA/CSA, the processing circuitry is configured to determine the apnea event cannot be characterized as one of a normal event, OSA event, a CSA event, or a combination OSA/CSA event from at least one of the one or more biomarkers.

15. The system of claim 6, wherein the therapy delivery circuitry is configured to be coupled to a first lead comprising a first plurality of electrodes located along a distal portion of the first lead, the distal portion of the first lead being configured to be implanted within musculature of a tongue of a patient.

16. The system of claim 15, wherein the therapy delivery circuitry is configured to be coupled to a second lead comprising a second plurality of electrodes located along a distal portion of the second lead, the distal portion of the second lead being configured to be implanted intravascularly proximate to a phrenic nerve within the patient.

17. A computer-readable storage medium storing instructions thereon that when executed cause one or more processors to:
  detect an apnea event based on one or more physiological signals;
  determine that the apnea event cannot be characterized as one of a normal, OSA (obstructive sleep apnea), CSA (central sleep apnea), or combination OSA/CSA event; and
  control therapy delivery circuitry to deliver a particular electrical stimulation as a default based on the determination that the apnea event cannot be characterized as a normal event, an OSA event, a CSA event, or combination OSA/CSA events.

18. The computer-readable storage medium of claim 17, wherein the instructions that cause the one or more processors to determine the apnea event cannot be characterized as one of a normal event, OSA event, a CSA event, or a combination OSA/CSA event comprise instructions that cause the one or more processors to determine the apnea event cannot be characterized as one of a normal event, OSA event, a CSA event, or a combination OSA/CSA event based on a frequency spectrum or a morphology of the one or more physiological signals.

19. The computer-readable storage medium of claim 17, wherein the one or more physiological signals comprise one or more of a motion signal, a cardiac electrical signal, or a bioimpedance signal.

20. The computer-readable storage medium of claim 17, further comprising instructions that cause the one or more processors to control the therapy delivery circuitry to be in an off state prior to the detection of the apnea event.

* * * * *